United States Patent
Coppersmith et al.

(10) Patent No.: US 9,357,906 B2
(45) Date of Patent: Jun. 7, 2016

(54) SURGICAL ILLUMINATION DEVICES AND METHODS THEREFOR

(71) Applicant: Engineered Medical Solutions Company LLC, Phillipsburg, NJ (US)

(72) Inventors: Daniel Coppersmith, Phillipsburg, NJ (US); Maximilian Linder, Phillipsburg, NJ (US); Michael H. El Kazzaz, Easton, PA (US)

(73) Assignee: Engineered Medical Solutions Company LLC, Phillipsburg, NJ (US)

( * ) Notice: Subject to any disclaimer, the term of this patent is extended or adjusted under 35 U.S.C. 154(b) by 125 days.

(21) Appl. No.: 14/254,459

(22) Filed: Apr. 16, 2014

(65) Prior Publication Data
US 2015/0297069 A1  Oct. 22, 2015

(51) Int. Cl.
*B60Q 1/06* (2006.01)
*F21V 29/00* (2015.01)
*A61B 1/06* (2006.01)
*A61B 1/12* (2006.01)

(52) U.S. Cl.
CPC .............. *A61B 1/0684* (2013.01); *A61B 1/0676* (2013.01); *A61B 1/128* (2013.01)

(58) Field of Classification Search
CPC .............. A61B 1/0684; A61B 1/00078; A61B 1/00096; A61B 1/00114; A61B 1/0676; A61B 1/128; F21V 29/503; F21V 29/70; F21V 29/71
See application file for complete search history.

(56) References Cited

U.S. PATENT DOCUMENTS

| | | | |
|---|---|---|---|
| 6,428,180 B1 | 8/2002 | Karram et al. | |
| 6,897,486 B2 | 5/2005 | Loh | |
| 6,974,234 B2 | 12/2005 | Galli | |
| 7,083,305 B2 | 8/2006 | Galli | |
| 7,207,695 B2 | 4/2007 | Coushaine et al. | |
| 7,270,439 B2 | 9/2007 | Horrell et al. | |
| 7,331,691 B2 | 2/2008 | Livesay et al. | |
| 7,540,634 B2 | 6/2009 | Belek | |
| 7,726,844 B2 | 6/2010 | Chen | |
| 7,963,678 B2 | 6/2011 | Chen | |
| 8,115,370 B2 | 2/2012 | Huang | |
| 8,226,272 B2 | 7/2012 | Chen | |
| 2005/0231983 A1 | 10/2005 | Dahm | |
| 2008/0002410 A1 | 1/2008 | Burton et al. | |
| 2008/0266840 A1 | 10/2008 | Nordmeyer et al. | |
| 2009/0287192 A1* | 11/2009 | Vivenzio | A61B 1/00105 606/1 |
| 2012/0065469 A1* | 3/2012 | Allyn | A61B 1/005 600/109 |
| 2012/0176803 A1* | 7/2012 | McLennan | F21K 9/00 362/373 |

* cited by examiner

*Primary Examiner* — Peggy Neils
*Assistant Examiner* — Alexander Garlen
(74) *Attorney, Agent, or Firm* — Doherty IP Law Group LLC

(57) ABSTRACT

A surgical illumination device includes a LED with a positive terminal, a negative terminal, and a heat transfer pad. A flexible circuit has first and second electrically conductive traces extending from a proximal end to a distal end thereof. The first conductive trace is electrically interconnected with the positive terminal, the second conductive trace is electrically interconnected with the negative terminal, and a heat transfer window on the flexible circuit is aligned with the heat transfer pad. The illumination device includes a heat sink having a distal end with a distal end face. A thermally conductive adhesive pad is disposed between the LED and the distal end face of the heat sink. The thermally conductive adhesive pad is aligned with the heat transfer window of the flexible circuit and the heat transfer pad of the LED base.

19 Claims, 32 Drawing Sheets

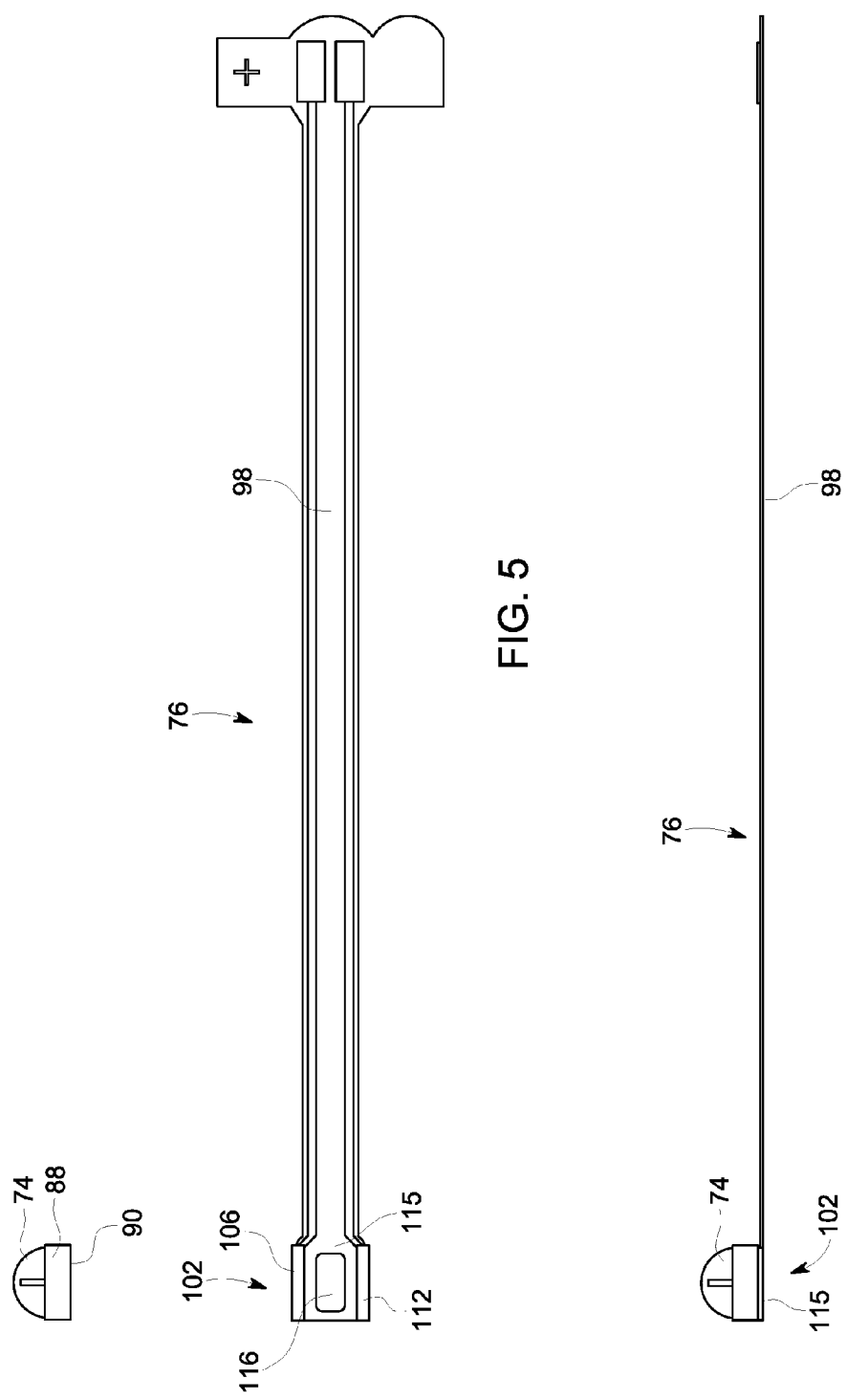

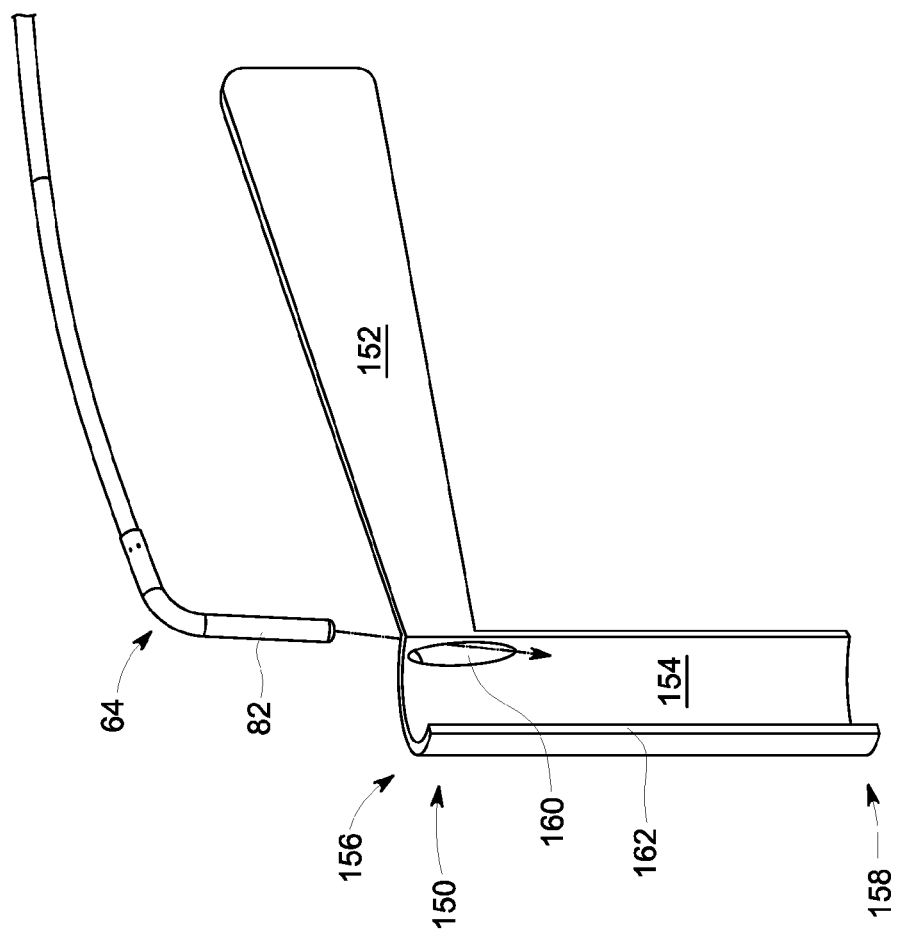

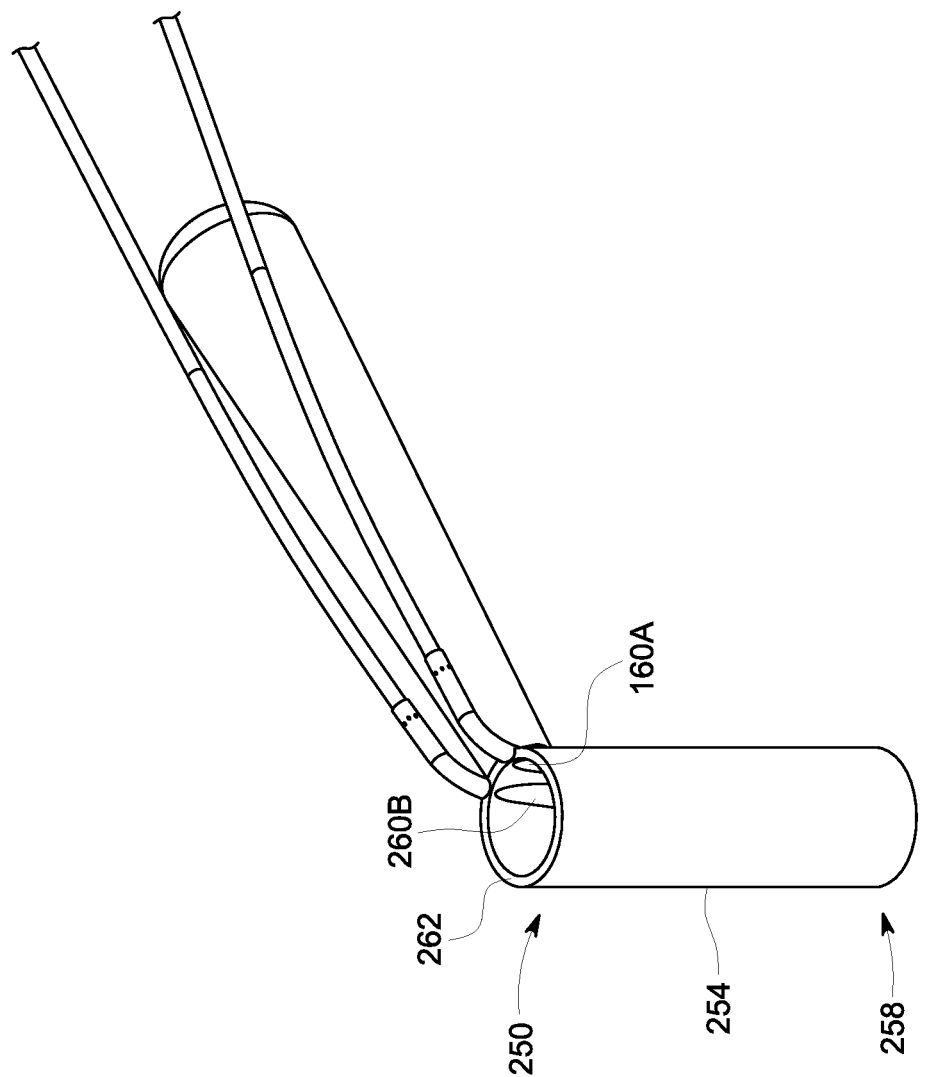

SURGICAL ILLUMINATION DEVICES AND METHODS THEREFOR

BACKGROUND OF THE INVENTION

1. Field of the Invention

The present invention is generally related to illumination and is more specifically related to surgical illumination devices used during medical examinations and surgical procedures.

2. Description of the Related Art

Ambient illumination is often inadequate for conducting safe and efficacious medical examinations and surgical procedures. Regardless of the intensity of the ambient lighting, shadows cast by medical personnel and/or other objects in a room (e.g., draperies) may prevent proper illumination of an examination site or surgical site. Moreover, when a surgical procedure is conducted inside a body cavity, providing sufficient lighting is even more difficult to achieve.

Illumination devices inserted into body cavities must be safe, reliable, capable of being sterilized, capable of operating with other surgical instruments, and be easy for a physician to manipulate. Critical specification features for such illumination devices typically include the brightness of the light, the amount of heat generated by the light, battery life, the shelf life of the device, ease of use with and without other devices, and affordability. For example, a light source may generate excessive heat that causes tissue damage a patient or injures a member of a medical team. Thus, it is desirable to have an illumination device that efficiently removes heat from the light source to avoid excessive temperatures that may damage tissue or injure medical personnel.

It is also desirable to have an illumination device that is user friendly, and that is capable of being quickly moved, mounted, dismounted, and remounted as needed for safely and efficiently completing medical procedures.

There have been a number of advances in illumination devices used for medical examinations and surgical procedures. For example, U.S. Pat. No. 6,428,180 to Karram et al. discloses a compact, self-powered, selectively-mountable lighting unit that provides light directable by a user to an operation site in a confined space to enable the user to operate a tool therein. The lighting unit is detachably mountable in a variety of ways either to a user-selected location on any suitable surgical instrument, or at the user's option to an adjacent location within the confined space, to facilitate well-lit and accurate viewing thereat. The lighting unit may be adapted to provide lighting of selected frequency, in an adjustable focus ranging from substantially diffuse light to a tightly focused beam. The lighting unit is designed to be mounted to surgical tools that are not specifically designed to be attached to lighting units.

U.S. Pat. No. 7,270,439 to Horrell et al. discloses a compact, self-contained lighting system that is attachable to a surgical tool to enable a user to selectively direct light at a site where the tool is to be applied. The system has a power unit that contains a power cell, a malleable electrical connection element, and a light-emitting element powered thereby to emit high intensity white light. The system ensures against tissue damage due to inadvertent overheating by continuously removing byproduct heat from the light-emitting element, via the connection element, to the power unit with portions of each of these components serving as respective heat sinks and/or as thermal conduits to facilitate this process. The removed heat is transferred in a proximal direction to a heat sink located in the handle part of the device.

U.S. Patent Application Publication No. 2008/0266840 discloses an illumination device having an electrically powered LED light source, a flexible boom having a first end on which the LED is mounted, a housing attached to a second end of the flexible boom opposite to the first end, an electric battery located within the housing, the battery being operatively associated with the LED for providing power thereto, a controller electrically connected to the battery and the LED for controlling the electrical power provided to the LED, and a switch mounted on the device and in communication with the controller so as to provide a signal to the controller when the switch is actuated. The controller is actuated by the switch to control the electrical power to the LED light source for turning the LED on and off.

In spite of the above advances, there remains a need for improved surgical illumination devices that have small cross-sectional footprints at the distal ends of the devices for being minimally invasive during medical examinations and surgical procedures. There also remains a need for surgical illumination devices that efficiently remove heat from the light sources at the distal ends of the devices so as to avoid tissue damage and/or problems associated with excessive heat. In addition, there remains a need for surgical illumination devices that may be coupled to a broad array of surgical tools to provide reliable illumination at examination sites and surgical sites. Moreover, there remains a need for surgical illumination devices that are versatile and that may be used in a broad range of surgical environments.

SUMMARY OF THE INVENTION

In one embodiment of the present invention, a surgical illumination device preferably includes a light emitting diode (LED) including a base having a bottom surface with a positive terminal, a negative terminal, and a heat transfer pad, and a flexible circuit including a flexible dielectric substrate with a proximal end, a distal end, and first and second electrically conductive traces extending from the proximal end to the distal end. In one embodiment, the distal end of the flexible dielectric substrate preferably includes the first conductive trace electrically interconnected with the positive terminal of the LED, the second conductive trace electrically interconnected with the negative terminal of the LED, and a heat transfer window aligned with the heat transfer pad of the LED base. The illumination device preferably includes a heat sink having a proximal end and a distal end with a distal end face, and a thermally conductive adhesive pad disposed between the distal end of the dielectric substrate and the distal end face of the heat sink for securing the LED and the distal end of the dielectric substrate to the distal end face of the heat sink. The thermally conductive adhesive pad is desirably aligned with the heat transfer window of the dielectric substrate and the heat transfer pad of the LED base.

In one embodiment, the distal end of the dielectric substrate preferably includes a LED mounting pad having a top surface and a bottom surface, whereby the first and second conductive traces are accessible at the top surface of the LED mounting pad, and whereby the heat transfer window extends from the top surface to the bottom surface of the LED mounting pad. In one embodiment, the heat transfer pad of the LED base is desirably located between the positive and negative terminals, and the heat transfer window of the LED mounting pad is located between the first and second conductive traces. In one embodiment, the LED base preferably has an outer perimeter and the LED mounting pad has an outer perimeter that matches the outer perimeter of the LED base.

In one embodiment, the heat sink has an elongated flat surface that extends from the distal end face to the proximal end of the heat sink. The LED mounting pad of the dielectric substrate is preferably secured over the distal end face of the heat sink and an intermediate section of the dielectric substrate overlies the elongated flat surface of the heat sink. In one embodiment, the distal end face of the heat sink is perpendicular to the elongated flat surface of the heat sink. In one embodiment, the heat sink comprises a conductive metal such as copper or aluminum. In one embodiment, the LED base covers an area of about 6 $mm^2$, the distal end face of the heat sink covers an area of about 7-9 $mm^2$, and the heat sink has a length of about 35-36 mm. In one embodiment, the heat sink has a length that is about 10× greater than the cross-sectional diameter at the distal end face of the heat sink and the LED base is mounted onto the distal end face and has a smaller footprint than the distal end face of the heat sink.

In one embodiment, the distal end of the heat sink preferably includes an edge located between the distal end face and the elongated flat surface of the heat sink. When the LED and LED mounting base are secured to the distal end face of the heat sink, the flexible dielectric substrate is desirably folded over the edge so that an intermediate section of the flexible dielectric substrate extends toward the proximal end of the heat sink.

In one embodiment, the distal end face of the heat sink defines a flat surface and the proximal end of the heat sink comprises a proximal end face that is flat. The proximal end of the heat sink preferably has a proximal edge located between the proximal end face and the elongated flat surface of the heat sink. In one embodiment, the proximal end of the flexible dielectric substrate is folded over the proximal edge of the heat sink.

In one embodiment, the heat sink does not extend all the way back to the housing at the proximal end of the surgical illumination device, which preferably enhances the flexibility of the distal end of the device. As such, in one embodiment, the heat sink is preferably not in thermal communication with the housing. In one embodiment, the heat sink desirably extends only part of the way toward the housing. In one embodiment, the proximal end of the heat sink terminates where it is connected to the distal end of a flexible power wire.

In one embodiment, the illumination device preferably includes an elongated tube, such as a stainless steel tube, having a proximal end, a distal end, and an elongated conduit extending from the proximal end to the distal end. In one embodiment, the LED, the flexible circuit and the heat sink are disposed inside the elongated tube with the LED being located adjacent the distal end of the elongated tube for emitting light at the distal end of the elongated tune. In one embodiment, an optical lens is secured to the distal end of the elongated tube for covering the LED.

In one embodiment, the elongated tube desirably includes an indented section that projects into the elongated conduit for controlling the orientation of the heat sink inside the elongated tube. In one embodiment, the elongated flat surface of the heat sink desirably faces toward the indented section of the elongated tube for limiting rotation of the heat sink about the longitudinal axis of the heat sink.

In one embodiment, the elongated tube and the heat sink are bent between the proximal and distal ends thereof, with the indented section of the bent elongated tube being located on the concave side of the bent elongated tube and the convexly curved side of the bent elongated tube facing away from the indented section.

In one embodiment, the surgical illumination device preferably includes a flexible power cord that is electrically interconnected with the first and second conductive traces of the flexible circuit. In one embodiment, a distal end of the flexible power cord is inserted into an opening at the proximal end of the elongated tube. The flexible power cord may include a first conductive wire having a non-conductive outer cladding, the first conductive wire having a proximal end, and a distal end electrically interconnected with the first conductive trace at the proximal end of the flexible dielectric substrate, and a second conductive wire having a non-conductive outer cladding, the second conductive wire having a proximal end, and a distal end electrically interconnected with the second conductive trace at the proximal end of the flexible dielectric substrate.

In one embodiment, the surgical illumination device desirably includes a printed circuit board electrically interconnected with the first and second conductive wires, whereby the printed circuit board preferably includes electronic components for controlling operation of the LED and at least one switch for activating the LED. In one embodiment, the printed circuit board may include electronic components (e.g., a microprocessor) for controlling operation of one or more LEDs electrically interconnected with the printed circuit board. In one embodiment, the printed circuit board includes electronic components that safeguard against the temperature of any of the LEDs exceeding a predetermined temperature (e.g., 46-48 degrees Celsius), which may cause tissue necrosis. In one embodiment, if one of the LED fails, the printed circuit board does not send the remaining power to the other LEDs that remain on-line thereby preventing any of the operating LEDs from becoming too hot and exceeding the predetermined temperature.

In one embodiment, a surgical illumination device preferably includes a housing having a circuit board, a power source, and a switch for activating the surgical illumination device, a flexible power line having a proximal end electrically interconnected with the circuit board and a distal end remote therefrom, and a distal tip secured to the distal end of the flexible power line. In one embodiment, the distal tip preferably includes a LED having a base including a bottom surface with a positive terminal, a negative terminal, and a heat transfer pad, and a flexible circuit including a flexible dielectric substrate with a proximal end, a distal end, and first and second electrically conductive traces extending from the proximal end to the distal end of the flexible dielectric substrate. The distal end of the flexible dielectric substrate desirably has the first conductive trace electrically interconnected with the positive terminal, the second conductive trace electrically interconnected with the negative terminal, and a heat transfer window aligned with the heat transfer pad of the LED base.

In one embodiment, the surgical illumination device preferably includes a heat sink having a proximal end, a distal end with a distal end face, and an elongated flat surface that extends from the distal end face to the proximal end of the heat sink, and a thermally conductive adhesive pad disposed between the distal end of the dielectric substrate and the distal end face of the heat sink for securing the LED and the distal end of the dielectric substrate to the distal end face of the heat sink, whereby the thermally conductive adhesive pad is aligned with the heat transfer window of the dielectric substrate and the heat transfer pad of the LED base. The illumination device preferably includes a stainless steel tube having a proximal end, a distal end, and an elongated conduit extending from the proximal end to the distal end, whereby the LED, the flexible circuit and the heat sink are disposed inside the stainless steel tube with the LED being located adjacent the distal end of the stainless steel tube, and an optical lens secured to the distal end of the stainless steel tube.

In one embodiment, the stainless steel tube preferably has an indented section that projects into the elongated conduit for controlling the orientation of the heat sink inside the stainless steel tube, whereby the elongated flat surface of the heat sink desirably faces toward the indented section of the stainless steel tube.

In one embodiment, the distal end of the dielectric substrate preferably includes a LED mounting pad having a top surface and a bottom surface, whereby the first and second conductive traces are accessible at the top surface of the LED mounting pad. In one embodiment, the heat transfer window desirably extends from the top surface to the bottom surface of the LED mounting pad, and the heat transfer pad of the LED base is located between the positive and negative terminals of the LED. In one embodiment, the heat transfer window of the LED mounting pad is preferably located between the first and second conductive traces, and the LED base has an outer perimeter and the LED mounting pad has an outer perimeter that matches the outer perimeter of the LED base.

These and other preferred embodiments of the present invention will be described in more detail below.

BRIEF DESCRIPTION OF THE DRAWINGS

FIGS. 5 and 6 show a method of assembling the light emitting diode of FIGS. 3A and 3B with the flexible circuit of FIGS. 4A and 4B, in accordance with one embodiment of the present invention.

FIGS. 16A-16B and 17A-17B show a method of using the surgical illumination device of FIG. 15 to illuminate a surgical tool, in accordance with one embodiment of the present invention.

DETAILED DESCRIPTION

Figure 1:
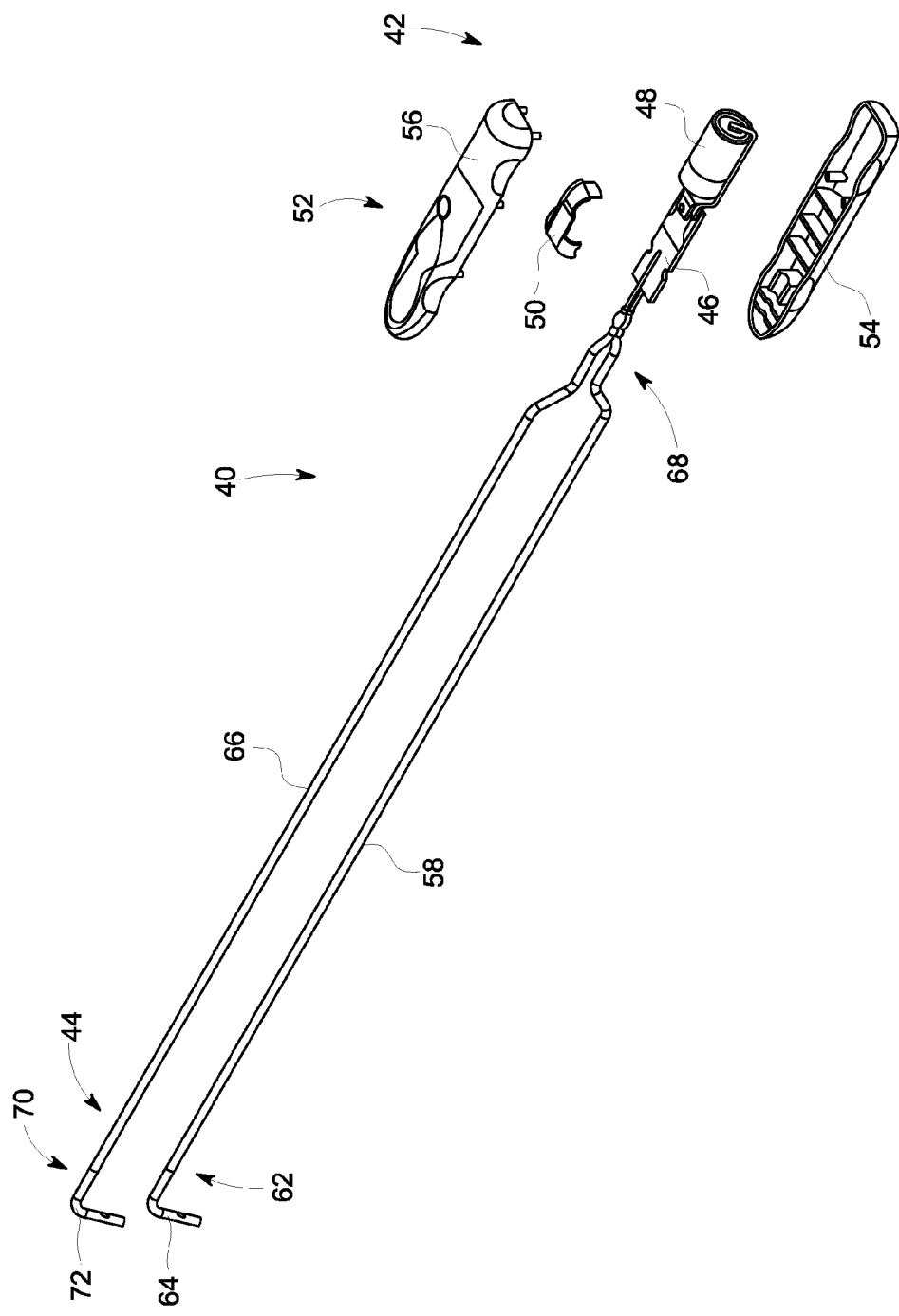
FIG. 1 shows a partially exploded view of a surgical illumination device, in accordance with one embodiment of the present invention.

Referring to FIG. 1, in one preferred embodiment of the present invention, a surgical illumination device 40 for surgical tools and surgical sites preferably has a proximal end 42 and a distal end 44. In one embodiment, the surgical illumination device preferably includes a circuit board 46, a power source 48, such as a lithium cell battery, and a circuit interrupt 50 that prevents the surgical illumination device from operating until the circuit interrupt has been removed. The surgical illumination device 40 preferably includes a housing 52 that encases the circuit board 46 and the power source 48. In one embodiment, the housing 52 desirably includes a lower housing part 54 and an upper housing part 56 that covers the lower housing part.

In one embodiment, the printed circuit board 46 preferably includes electronic components for controlling operation of the surgical illumination device 40. In one embodiment, the electronic components may include one or more microprocessors, switches, capacitors, resistors, diodes, and/or converters, etc.

In one embodiment, the surgical illumination device preferably includes a first flexible power line 58 having a proximal end 68 connected with the circuit board 46 and a distal end 62 having a first distal tip 64 with a first light emitting diode incorporated into the first distal tip. The surgical illumination device 40 preferably includes a second flexible power line 66 having a proximal end 68 connected with the circuit board 46 and a distal end 70 having a second distal tip 72 with a second light emitting diode incorporated into the second distal tip. In one embodiment, the surgical illumination device may have a single flexible power line with a single distal tip. In one embodiment, the surgical illumination device may have more than two flexible power lines and distal tips.

Figure 2:
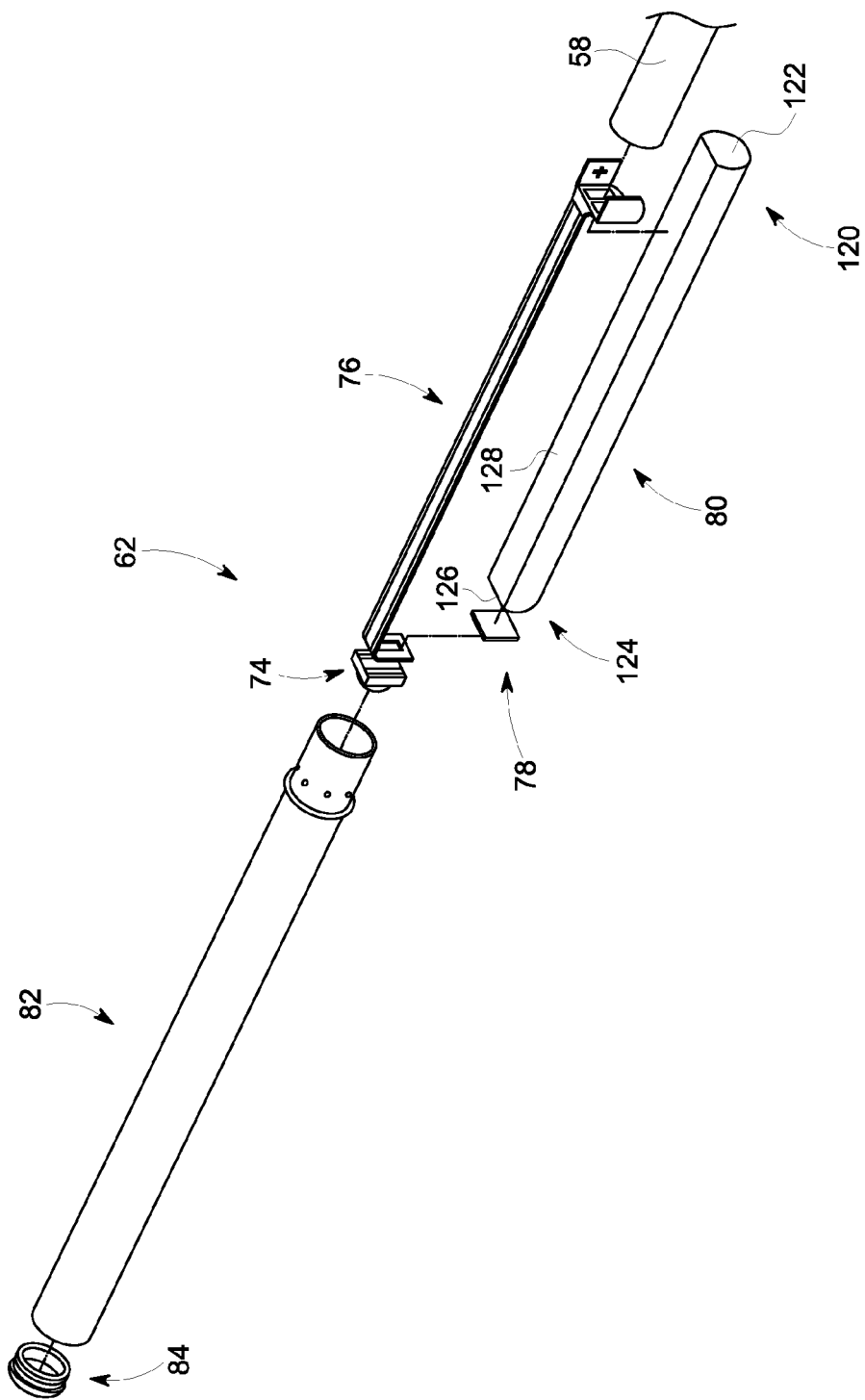
FIG. 2 shows an exploded view of a distal tip of the surgical illumination device of FIG. 1, in accordance with one embodiment of the present invention.

Referring to FIG. 2, in one embodiment, the first distal tip 64 (FIG. 1) at the distal end 62 of the first flexible power line 58 preferably includes a light emitting diode (LED) 74, a flexible circuit 76, a thermal pad 78 and a heat sink 80. In one embodiment, after the LED 74 is mounted onto the distal end of the flexible circuit 76, the LED/flexible circuit subassembly is secured to a distal end face of the heat sink 80 by a thermally conductive adhesive pad 78 that is disposed between an underside of the flexible circuit 76 and the distal end face of the heat sink 80. In one embodiment, the thermally conductive adhesive pad 78 transfers heat from the LED 74 to the distal end face of the heat sink 80.

In one embodiment, the LED/flexible circuit/heat sink subassembly is inserted into an elongated outer tube 82, such as a stainless steel outer tube. The distal end of the outer tube 82 is preferably covered by an optical lens 84. In one embodiment, the optical lens is preferably affixed to the distal end of the elongated outer tube, such as by gluing or soldering the optical lens to the elongated outer tube. In one embodiment, the optical lens is affixed to the elongated outer tube by inserting the lens into an open distal end of the elongated outer tube, whereupon the lens is swaged onto the tube such as by crimping the elongated outer tube for forming a permanent connection between the optical lens and the elongated outer tube. In one embodiment, the proximal end of the flexible circuit 76 is desirably electrically interconnected with the distal end of the first flexible power line 58. In one embodiment, the proximal end of the stainless steel outer tube 82 is crimped onto the distal end of the first flexible power line 58 for securing the outer tube 82 to the first flexible power line 58.

Figure 3B:
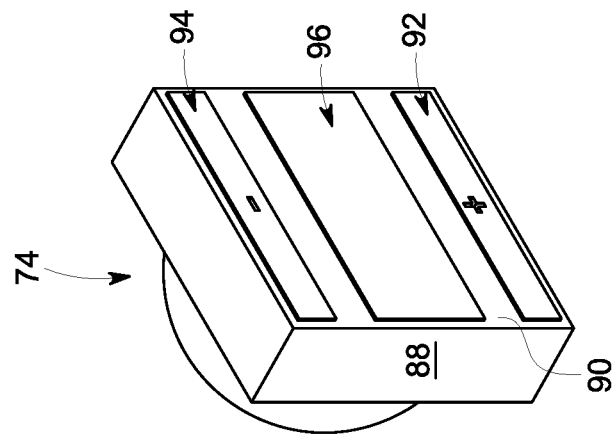
FIGS. 3A and 3B show a light emitting diode for the surgical illumination device of FIG. 1, in accordance with one embodiment of the present invention.
Figure 3A:
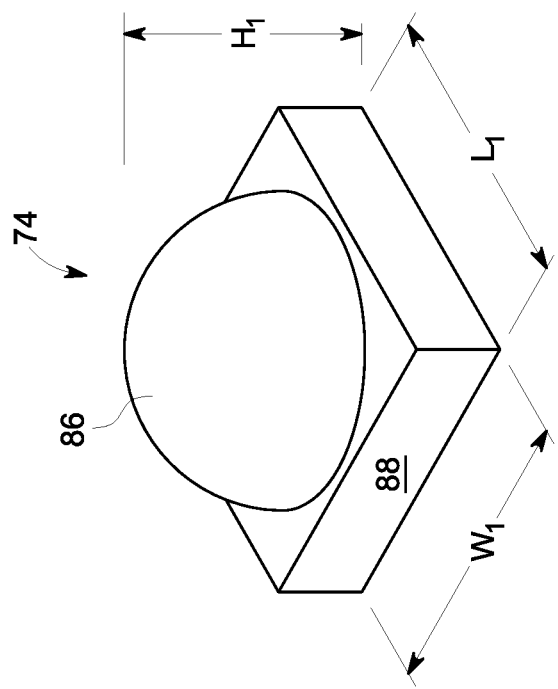

Referring to FIGS. 3A and 3B, in one embodiment, the LED 74 preferably includes a transparent or clear dome 86 and a base 88 having an outer perimeter. In one embodiment, the LED 74 is a light emitting diode sold by Cree, Inc. of Durham, N.C., such as LED model XB-D. In one embodiment, the LED is preferably model XB-D 1221m Cool White LED sold by Cree, Inc. In one embodiment, the base 88 has a length $L_1$ of about 2 -3 mm and more preferably about 2.45 mm, and a width $W_1$ of about 2-3 mm and more preferably about 2.45 mm. In one embodiment, the LED 74 has a height $H_1$ of about 1.50-2.0 mm and more preferably about 1.84 mm. In one embodiment, the LED may have a larger or a smaller footprint than the Cree LED model XB-D described above. For example, in one embodiment, the LED may be Cree, Inc.'s model XQ having a 1.6 mm×1.66 mm base or Phillips Lumileds model LXZ25770 having a 1.6 mm×2.0 mm base.

Referring to FIG. 3B, in one embodiment, the LED base 88 has a bottom surface 90 including a positive terminal 92, a negative terminal 94, and a thermally conductive pad 96 located between the positive terminal and the negative terminal. In one embodiment, the heat generated by the LED 74 is removed from the LED via the thermally conductive pad 96. In one embodiment, the LED base may have two or more thermally conductive pads that are spaced from one another. In one embodiment, the thermally conductive pad(s) may be at the outer perimeter of the base 88 and the positive and negative terminals may be located inside the thermally conductive pad(s).

Figure 4A:
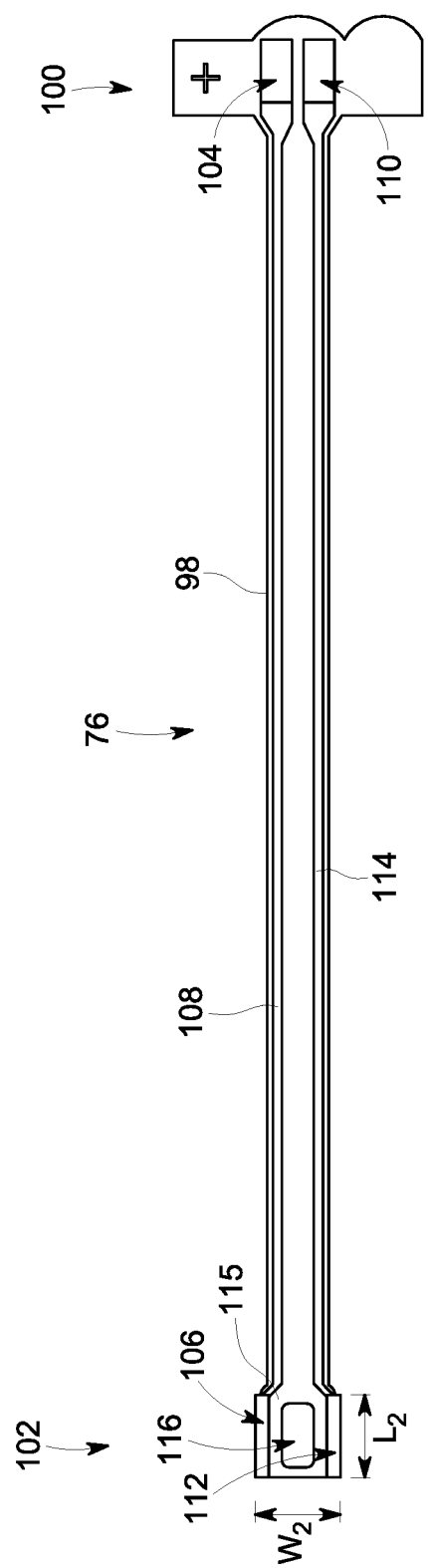
FIGS. 4A and 4B show a flexible circuit for the surgical illumination device of FIG. 1, in accordance with one embodiment of the present invention.
Figure 4B:
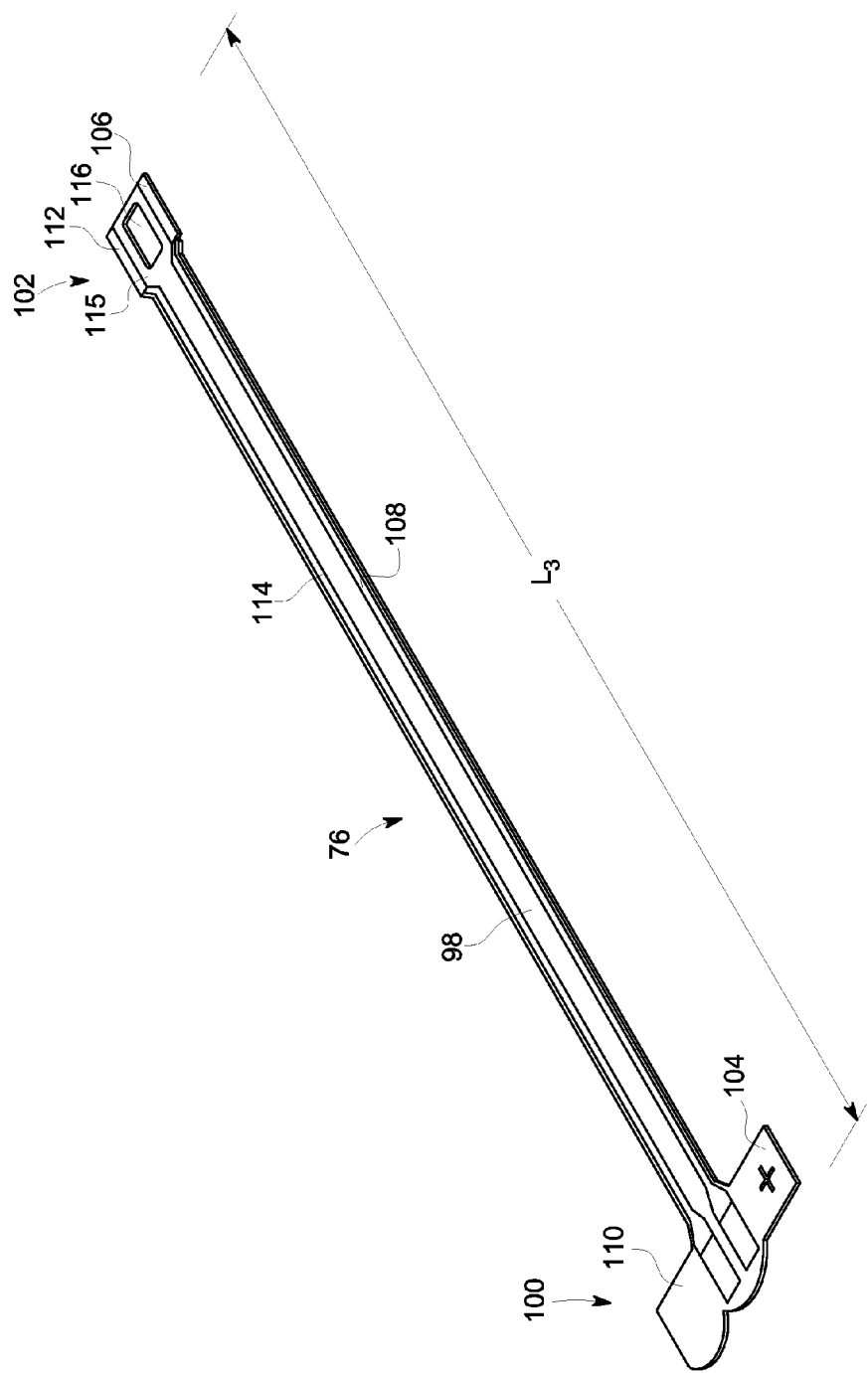

Referring to FIGS. 4A and 4B, in one embodiment, a surgical illumination device preferably includes a flexible circuit 76 that provides electrical power for the LED. In one embodiment, the flexible circuit 76 desirably includes a dielectric substrate 98 having a proximal end 100 and a distal end 102. The flexible circuit 76 preferably has a first positive terminal 104 located at the proximal end 100 of the dielectric substrate 98 and a second positive terminal 106 located at the distal end 102 of the dielectric substrate 98. A first conductive trace 108 electrically interconnects the first and second positive terminals 104, 106. The flexible circuit 76 preferably has a first negative terminal 110 located at the proximal end 100 of the dielectric substrate 98 and a second negative terminal 112 located at the distal end 102 of the dielectric substrate 98. A second conductive trace 114 electrically interconnects the first and second negative terminals 110, 112.

In one embodiment, the distal end 102 of the dielectric substrate 76 preferably includes a LED mounting base 115 having a heat transfer window 116 formed therein. In one embodiment, the LED mounting base 115 has a length $L_2$ of about 2-3 mm and more preferably 2.45 mm and a width $W_2$ of about 2-3 mm and more preferably about 2.45 mm. In one embodiment, the outer perimeter of the LED mounting base preferably matches the outer perimeter of the LED base. In one embodiment, the footprint of the LED base matches the footprint of the LED mounting base. In preferred embodiment, the heat transfer window 116 is located between the second positive terminal 106 and the second negative terminal 112. As will be described in more detail herein, in one embodiment, when the LED 74 (FIGS. 3A and 3B) is electrically interconnected with the positive and negative terminals 106, 112 at the distal end of the dielectric substrate 98, the thermal pad 96 at the bottom surface of the LED base is preferably aligned with the heat transfer window 116 at the distal end of the flexible circuit 76 for facilitating the passage of heat generated by the LED through the heat transfer window.

In one embodiment, the positive and negative terminals of the LED are electrically interconnected with the flexible circuit using solder. In one embodiment, the positive and negative terminals of the LED are electrically interconnected with the flexible circuit using reflow soldering techniques.

Referring to FIG. 4B, in one embodiment, flexible dielectric substrate is flexible so that the LED mounting base 115 at the distal end 102 of the flexible circuit 76 may be folded over the distal end face of the heat sink 80 (FIG. 2). In one embodiment, the proximal end of the flexible dielectric substrate including the first positive terminal 104 and the first negative terminal 110 is foldable over a proximal end face at the proximal end of the heat sink 80 (FIG. 2). In one embodiment, the flexible circuit has a length $L_3$ of about 35-40 mm and more preferably about 38 mm. In one embodiment, the flexible circuit has a length that generally matches the length of the heat sink. In one embodiment, the flexible circuit may be longer than the heat sink and may extend all the way to the housing containing the printed circuit board.

Referring to FIG. 5, in one embodiment, the LED 74 is juxtaposed with the LED mounting base 115 at the distal end 102 of the flexible circuit 76. In one embodiment, the bottom surface 90 of the LED 74 is preferably abutted against the top surface of the LED mounting base 115 of the dielectric substrate 98 so that the positive terminal 92 (FIG. 3B) at the bottom surface of the LED base 88 is electrically interconnected with the second positive terminal 106 of the flexible circuit 76 and the negative terminal 94 (FIG. 3B) at the bottom surface of the LED base is electrically interconnected with the second negative terminal 112 of the flexible circuit. FIG. 6 shows the LED 74 secured onto the LED mounting base 115 at the distal end 102 of the dielectric substrate 98 of the flexible circuit 76. In one embodiment, the footprint of the LED base 88 generally matches the footprint of the LED mounting base 115 at the distal end 102 of the flexible circuit 76, which contains the second positive terminal 106, the second negative terminal 112 and the thermal transfer window 116 (FIG. 5).

Figure 7:
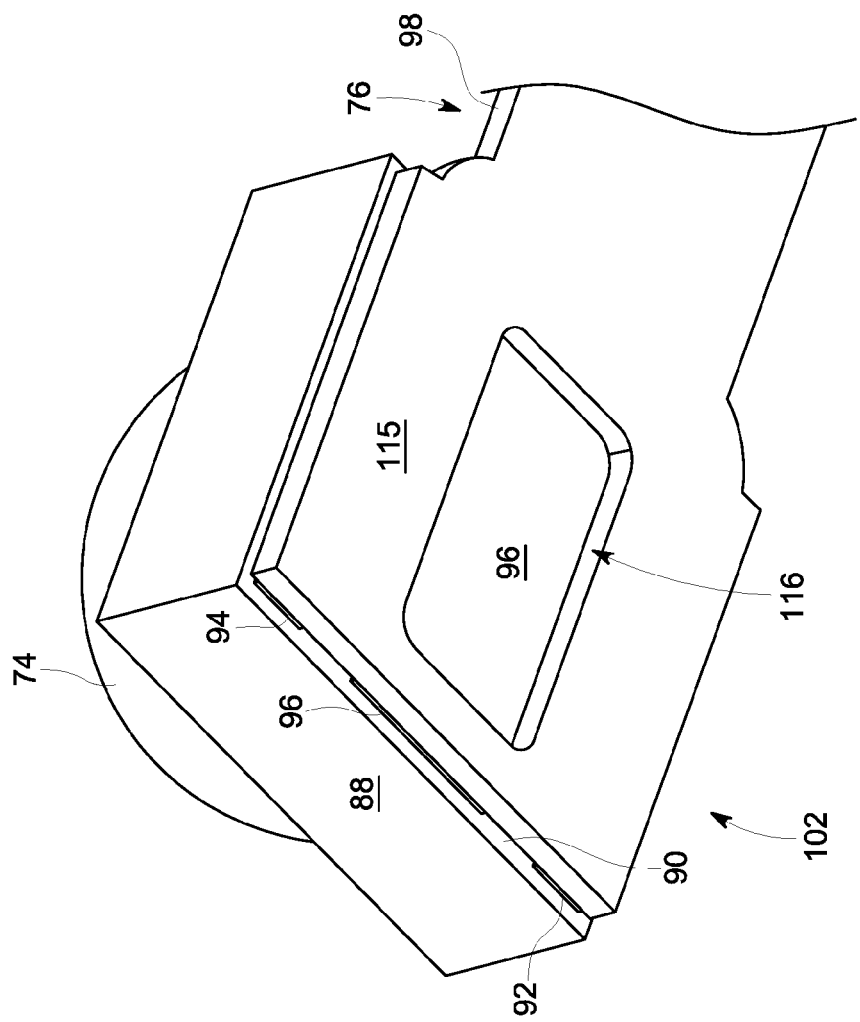
FIG. 7 shows a bottom perspective view of the light emitting diode and the flexible circuit of FIG. 6 after the light emitting diode has been secured atop the distal end of the flexible circuit, in accordance with one embodiment of the present invention.

Referring to FIG. 7, in one embodiment, the bottom surface 90 of the base 88 of the LED 74 is juxtaposed with the LED mounting base 115 at the distal end 102 of the dielectric layer 98 of the flexible circuit 76. The positive terminal 92 of the LED is electrically interconnected with the second positive terminal 106 of the flexible circuit, and the negative terminal 94 of the LED is electrically interconnected with the second negative terminal 112 of the flexible circuit. The thermal pad 96 accessible at the bottom surface of the LED base 88 is preferably aligned with the heat transfer window 116 of the LED mounting base 115 of the flexible circuit 76 so that heat may be transferred from the LED via the thermal transfer window 116. In one embodiment, the LED mounting base 115 has a square shape and the LED base 88 has a square shape.

Figure 8:
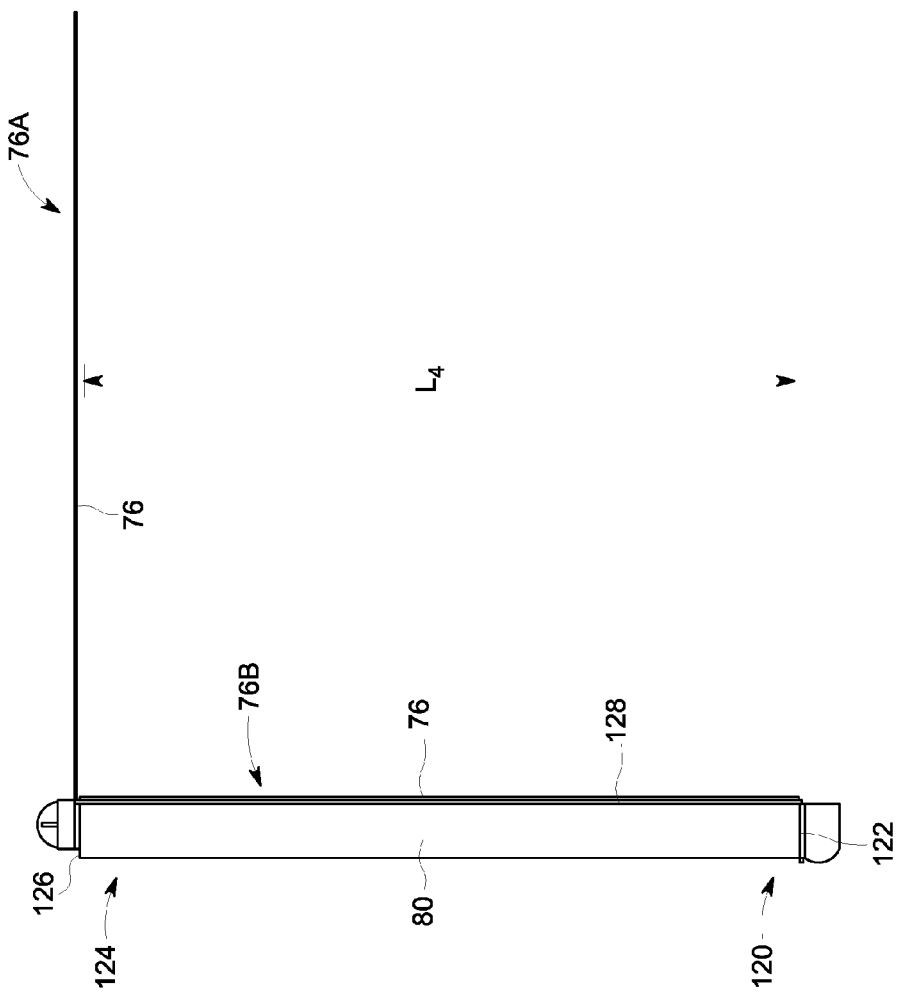
FIG. 8 shows the light emitting diode and the flexible substrate subassembly of FIGS. 6 and 7 secured to an elongated heat sink, in accordance with one embodiment of the present invention.
Figure 9:
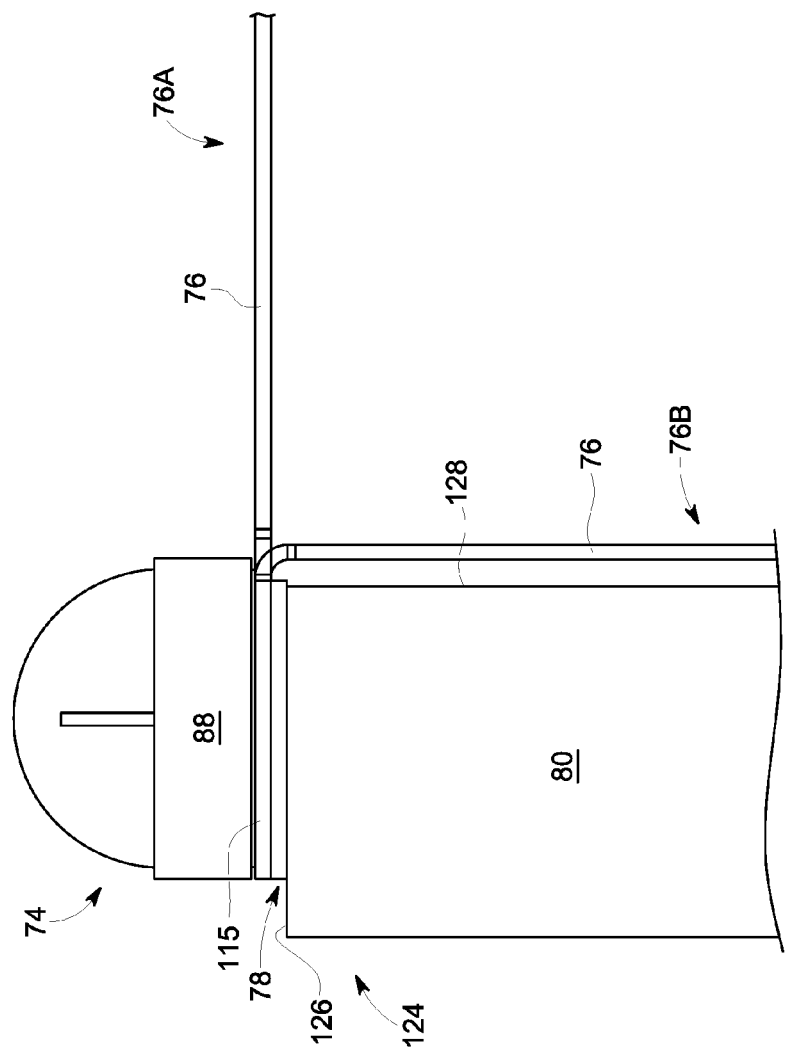
FIG. 9 shows a magnified view of the distal end of the heat sink shown in FIG. 8.

Referring to FIGS. 8 and 9, in one embodiment, a surgical illumination device preferably includes a heat sink 80 that is utilized for removing heat from the LED 74. In one embodiment, the heat sink 80 preferably has a proximal end 120 with a flat proximal face 122, and a distal end 124 with a flat distal face 126. The heat sink 80 is preferably made of a thermally conductive metal such as copper or aluminum. In a more preferred embodiment, the heat sink 80 is made of copper. The heat sink 80 preferably has a cylindrical shape having an outer diameter OD1 of about 3-4 mm and more preferably about 3.35 mm. The heat sink desirably has a length $L_4$ of about 30-40 mm and more preferably about 35 mm. Referring to FIGS. 2, 8 and 9, in one embodiment, the heat sink 80 desirably has elongated flat face 128 (FIG. 2) that extends along one side of the heat sink 80 from the flat proximal face 122 at the proximal end 120 of the heat sink to the flat distal face 126 at the distal end 124 of the heat sink. As will be described in more detail herein, the flat elongated face 128 that extends along the length of the heat sink provides space for the flexible circuit 76 when the heat sink and the flexible circuit are inserted into the stainless steel tube 82 (FIG. 2). The flat elongated face 128 also desirably orients the heat sink within the stainless steel tube as will be described in more detail herein.

Referring to FIGS. 8 and 9, in one embodiment, a thermally conductive adhesive pad 78 is positioned atop the flat distal face 126 at the distal end 124 of the heat sink 80 for securing the LED mounting base 115 to the distal end face of the heat sink 80. The base 88 of the LED 74 is aligned with the LED mounting base 115 and the thermally conductive adhesive pad 78 so that heat generated by the LED 74 may be efficiently transferred between the LED and the heat sink 80.

FIGS. 8 and 9 show the flexible circuit 76 in a first extended, unbent position 76A, and a second bent or folded position 76B in which the flexible circuit overlies the elongated flat face 128 of the heat sink 80. When the heat sink is inserted into the stainless steel tube, the flexible circuit is preferably folded over the elongated flat face 128 of the heat sink.

Figure 10:
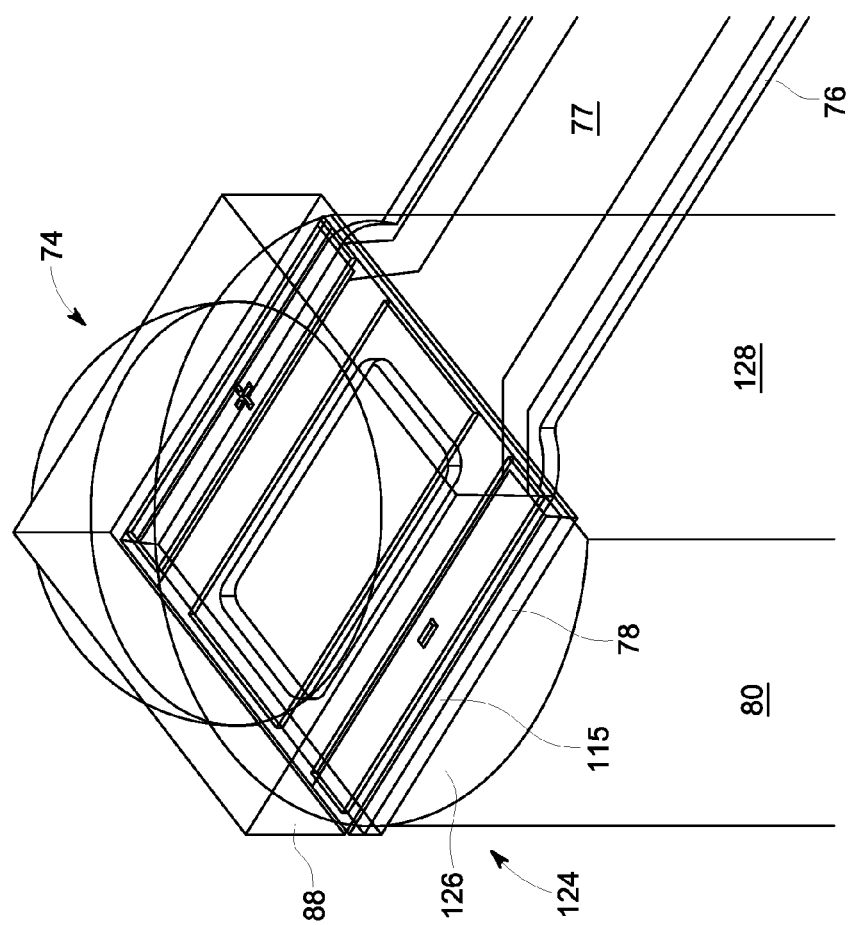
FIG. 10 shows a top perspective view of the assembly shown in FIG. 9.
Figure 11:
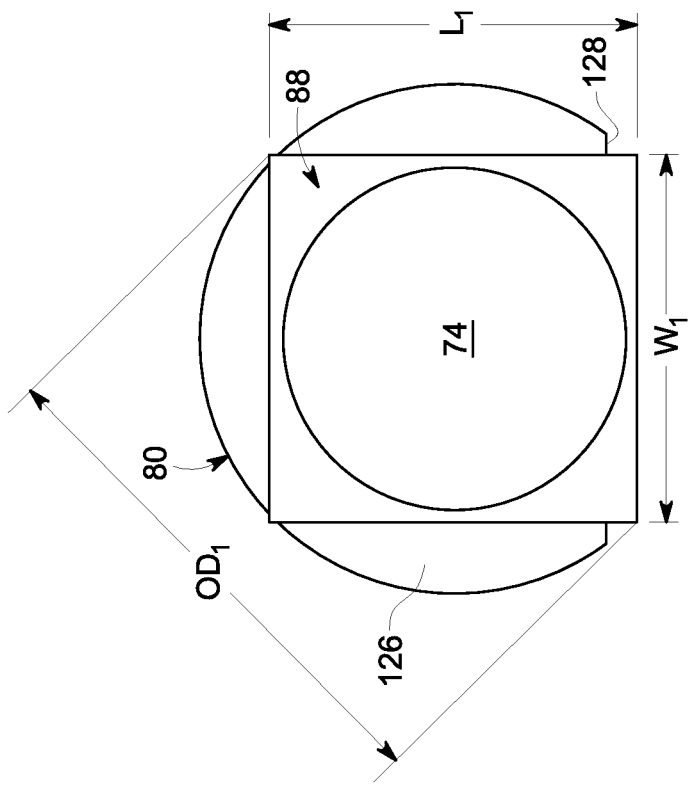
FIG. 11 shows a top plan view of the assembly shown in FIGS. 9 and 10.

Referring to FIGS. 10 and 11, in one embodiment, the base 88 of the LED 74 sits atop the LED mounting base 115 of the flexible circuit 76, which in turn, sits atop the thermally conductive adhesive pad 78 overlying the flat distal face 126 at the distal end 124 of the heat sink 80. The flexible circuit 76 is preferably aligned with the elongated flat face 128 of the heat sink 80 so that an intermediate section 77 of the flexible circuit 76, proximal to the LED mounting base 115, may be folded over the elongated flat face 128 for extending along the length of the heat sink (see position 76B in FIG. 9). Referring to FIG. 11, in one embodiment, the base 88 of the LED 74 has a length $L_1$ of about 2.45 mm and a width $W_1$ of about 2.45 mm. The flat face 126 at the distal end of the heat sink 80 has an outer diameter $OD_1$ of about 3.4 mm. In one embodiment, the LED base 88 is positioned atop the flat distal face 126 of the heat sink 80 so that the LED base 88 slightly overhangs the elongated flat face 128 of the heat sink 80, which facilitates folding the intermediate section 77 of the flexible circuit 76 over the elongated flat face 128.

Figure 12:
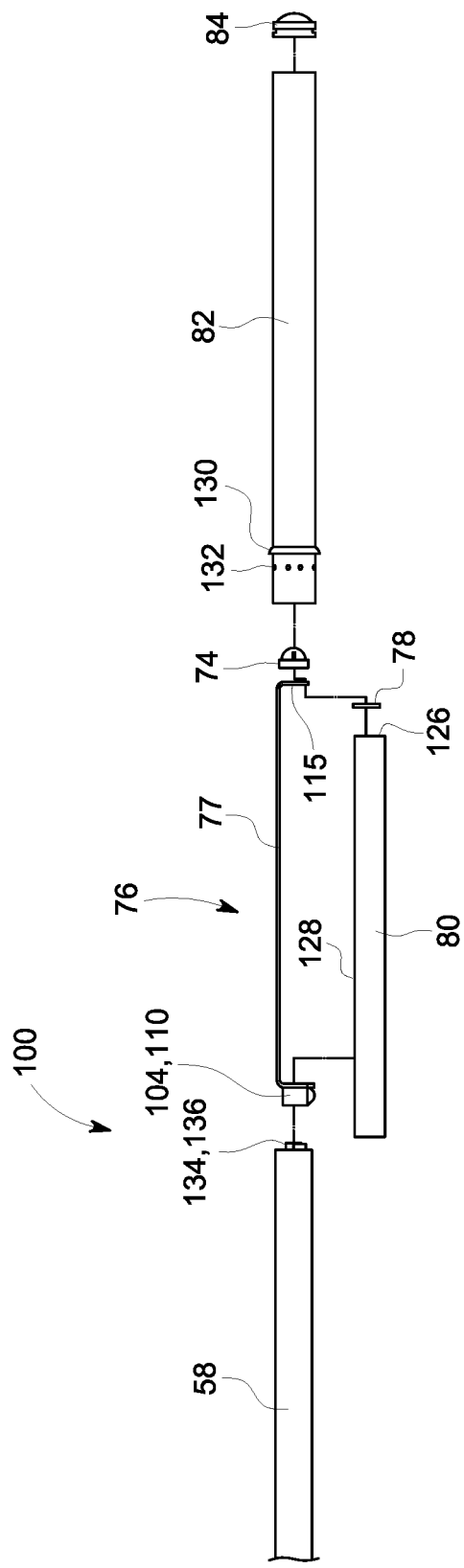
FIG. 12 shows a method of assembling a distal tip of a surgical illumination device, in accordance with one embodiment of the present invention.
Figure 13:
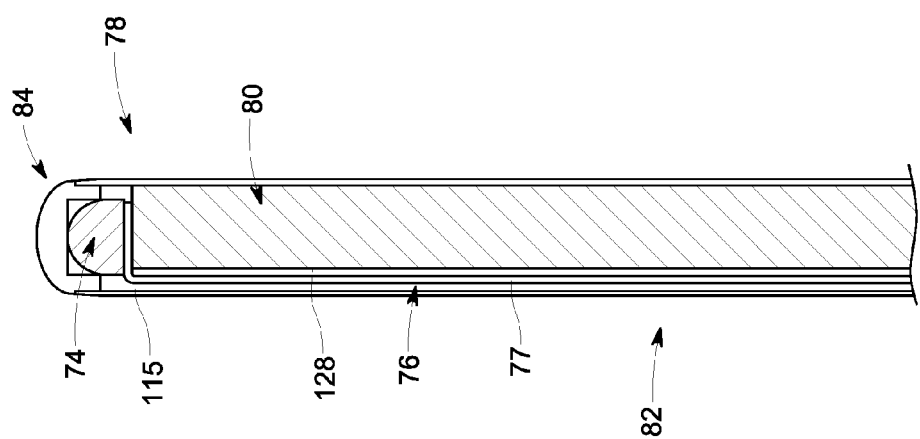
FIG. 13 shows a cross-sectional view of a distal tip of a surgical illumination device, in accordance with one embodiment of the present invention.

Referring to FIGS. 12 and 13, in one embodiment, the LED 74 is mounted onto the LED mounting base 115 at the distal end of the flexible circuit 76. The thermally conductive adhesive pad 78 is positioned between the flat distal face 126 at the distal end of the heat sink 80 and the LED mounting pad 115. The flexible circuit 76 is folded so that the intermediate section 77 of the flexible circuit 76 overlies the elongated flat face 128 of the heat sink 80. A subassembly including the LED 74, the thermally conductive adhesive pad 78, the flexible circuit 76 and the heat sink 80 is preferably inserted into an opening at the proximal end of the stainless steel tube 82, and the LED is advanced distally through the stainless steel tube 82 until it is positioned adjacent an opening at the distal end of the tube 82. The optical lens 84 is inserted into the opening at the distal end of the stainless steel tube 82 for covering the light emitting side of the LED 74.

Referring to FIG. 12, the proximal end of the stainless steel tube 82 preferably includes an annular stop 130 that extends around the outer perimeter of the tube. The annular stop 130 preferably stops distal movement of the tube when the tube is inserted into an opening formed in a surgical tool, as will be described in more detail herein. The tube 82 also desirably includes crimping projections 132 that are spaced from one another about the proximal end of the tube. The crimping projections 132 are preferably proximal to the annular stop 130. In one embodiment, after the proximal end of the first power wire 58 is inserted into the opening at the proximal end of the stainless steel tube 82, a crimping tool is used for engaging the crimping projections 132 for securing the tube 82 to the power wire 58.

Referring to FIG. 12, in one embodiment, the proximal end 100 of the flexible circuit 76 preferably includes the first positive contact pad 104 and the first negative contact pad 110 which are electrically interconnected with jacketed electrically conductive wires 134, 136, respectively, accessible at the distal end of the first flexible power line 58. In one embodiment, after the first flexible power line 58 is electrically interconnected with the conductive pads at the proximal end of the flexible circuit 76, the distal end of the first flexible power line 58 is inserted into an opening at the proximal end of the stainless steel tube 82. Referring to FIG. 12, a crimping tool may be used to crimp the crimping projections 132 to secure the first flexible power line 58 to the stainless steel tube 82. In one embodiment, the first flexible power line 58 is affixed to the stainless steel tube 82 by a wide variety of methodologies including but not limited to glues, adhesives, over molding techniques, edge rolling techniques, welding and/or ultrasonic welding.

Figure 14A:
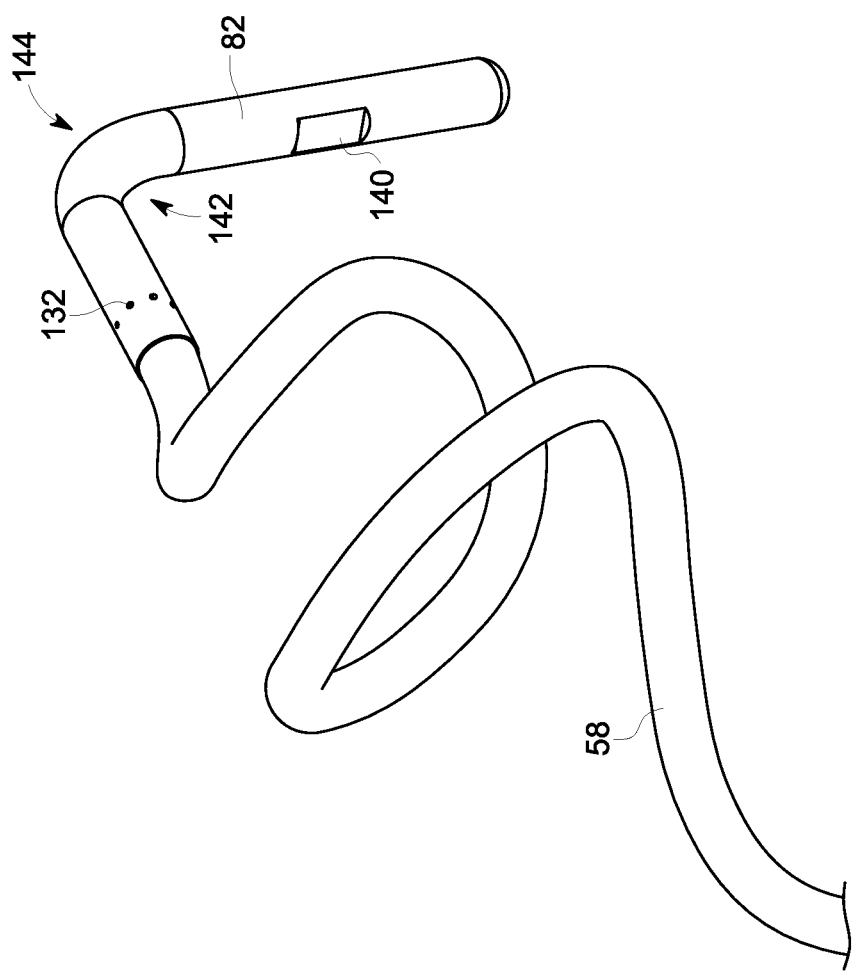
FIG. 14A shows a distal tip of a surgical illumination device, in accordance with one embodiment of the present invention.
Figure 14B:
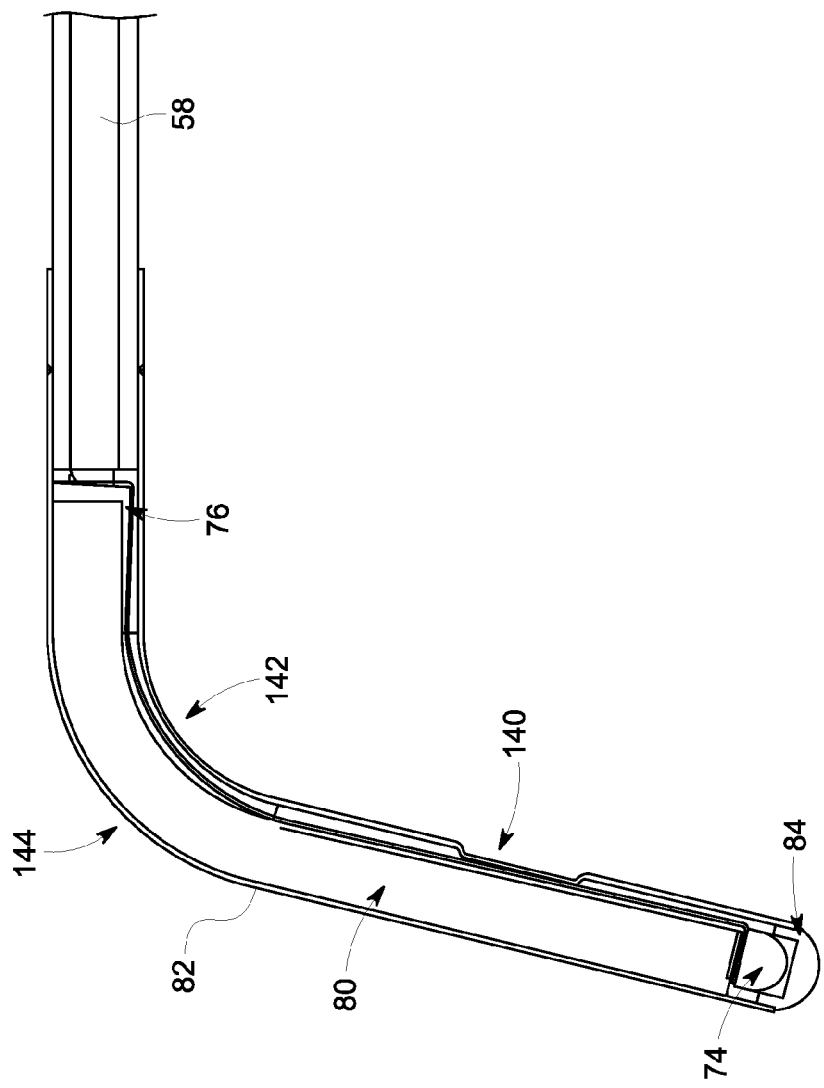
FIG. 14B shows a cross-sectional view of the distal tip of the surgical illumination device of FIG. 14A.

In one embodiment, it may be desirable to bend the stainless steel tube and the heat sink disposed inside the stainless steel tube. The stainless steel tube may be bent into a wide range of angles and/or curvatures to facilitate efficient use with a wide variety of surgical tools for illuminating the surgical tools and/or surgical sites. Referring to FIGS. 14A and 14B, in one embodiment, the stainless steel tube 82 has an orientation indent 140 formed therein that extends into the internal conduit of the tube. When the heat sink 80 is inserted into the stainless steel tube, the elongated flat face 128 of the stainless steel tube and the folded flexible circuit 76 are preferably oriented so that they oppose the orientation indent 140. In order to form a surgical illumination device having a curved distal tip, the stainless steel tube 82 and the heat sink 80 are preferably bent to form a concave surface 142 that is on the same side of the stainless steel tube as the orientation indent 140. The bent stainless steel tube also has a convexly curved surface 144 that faces away from the orientation indent 140. Although the present invention is not limited by any particular theory of operation, it is believed that using the orientation indent 140 for positioning the flexible circuit 76 on the concave curved side of the stainless steel tube 82 will prevent the flexible circuit 76 from being stretched. If the flexible circuit was positioned on the convex side of the curve, it would likely be stretched when bending the tube and the heat sink. It is desirably to not stretch the flexible circuit because stretching the flexible circuit may break an electrical interconnection and/or reduce the reliability of the flexible circuit. Thus, in one embodiment, using the orientation indent 140 preferably prevents the flexible circuit from being stretched.

Figure 15:
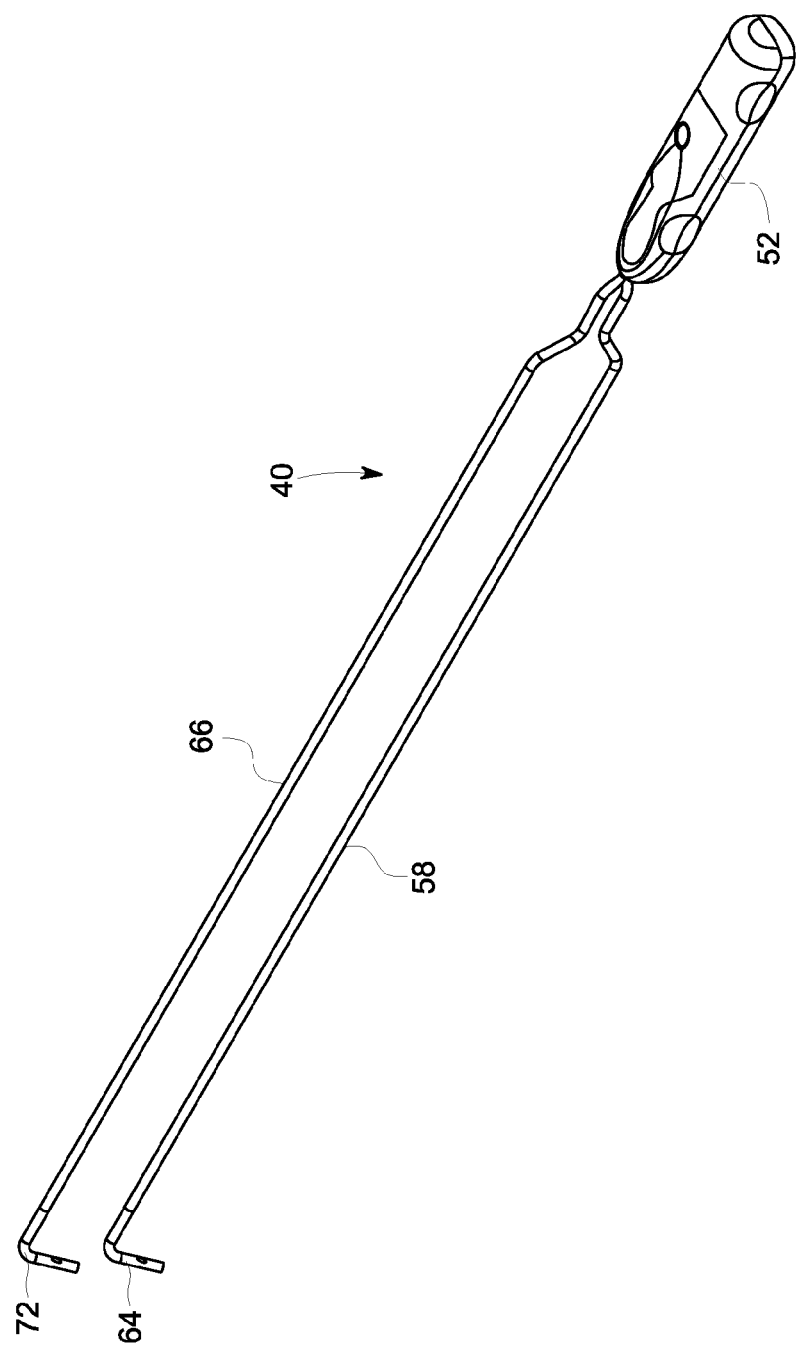
FIG. 15 shows a perspective view of a surgical illumination device having bent distal tips, in accordance with one embodiment of the present invention.

Referring to FIG. 15, in one embodiment, a surgical illumination device 40 for illuminating surgical tools and surgical sites preferably includes a first curved distal tip 64 at a distal end of a first flexible power line 58 and a second curved distal tip 72 at a distal end of a second flexible power line 66. In other embodiment, a surgical illumination tool may have only one power line with a single distal tip. Other embodiments may include three or more flexible power lines, each having a distal tip associated therewith. Each of the distal tips 64, 72 preferably has a LED light, respectively, that emits light from the distal-most ends of the tips. The surgical illumination device 40 preferably includes a housing 52 with an internally mounted circuit board that is used for driving the LEDs. The surgical illumination device preferably has an ON switch accessible at the outer surface of the housing 52 for activating the LEDs for use during a surgical procedure.

Figure 16B:
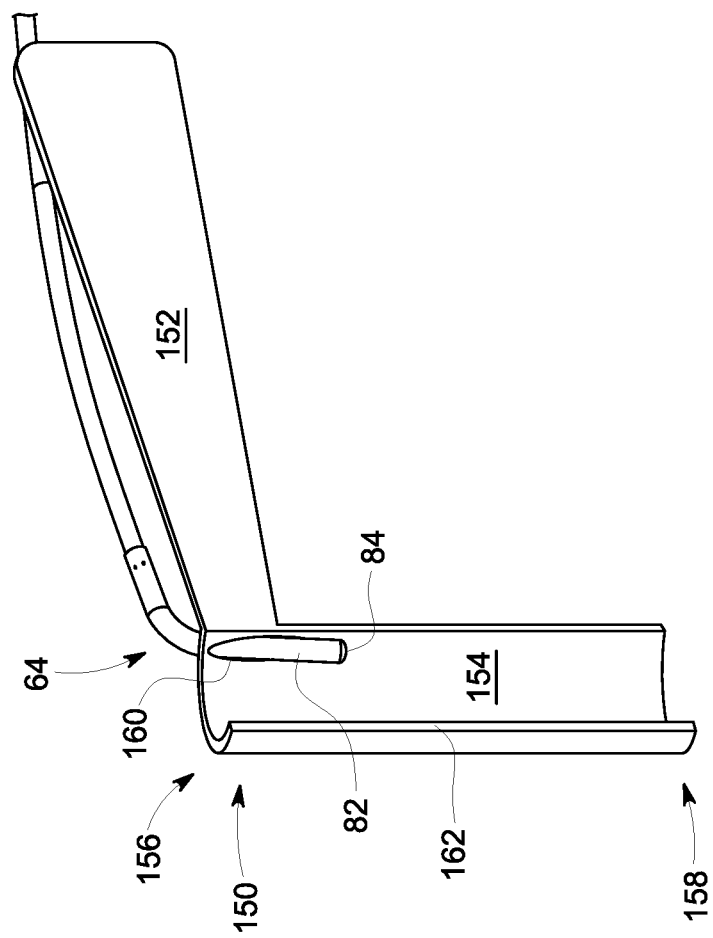

Referring to FIGS. 16A and 16B, in one embodiment, the surgical illumination device disclosed herein may be used to provide light for a surgical tool 150. In one embodiment, the surgical tool 150 has a handle 152, and includes a tubular element 154 having a proximal end 156 and a distal end 158. The surgical tool preferably has an elongated opening 160 formed therein that extends through the wall 162 of the tubular element 154, and which is adapted to secure a curved distal tip 64 that contains a LED. In one embodiment, the elongated opening 160 has a circular shaped cross section that matches the cylindrical shape of the stainless steel tube 82. In one embodiment, the curved distal tip 64 of a surgical illumination device is inserted into the elongated opening 160 for providing light inside the tubular element 154. In one embodiment, the optical lens 84 is preferably oriented toward the distal end of the tubular element 154 for directing the emitted light toward the distal end of the tool 150 (e.g., toward a surgical site).

Figure 17B:
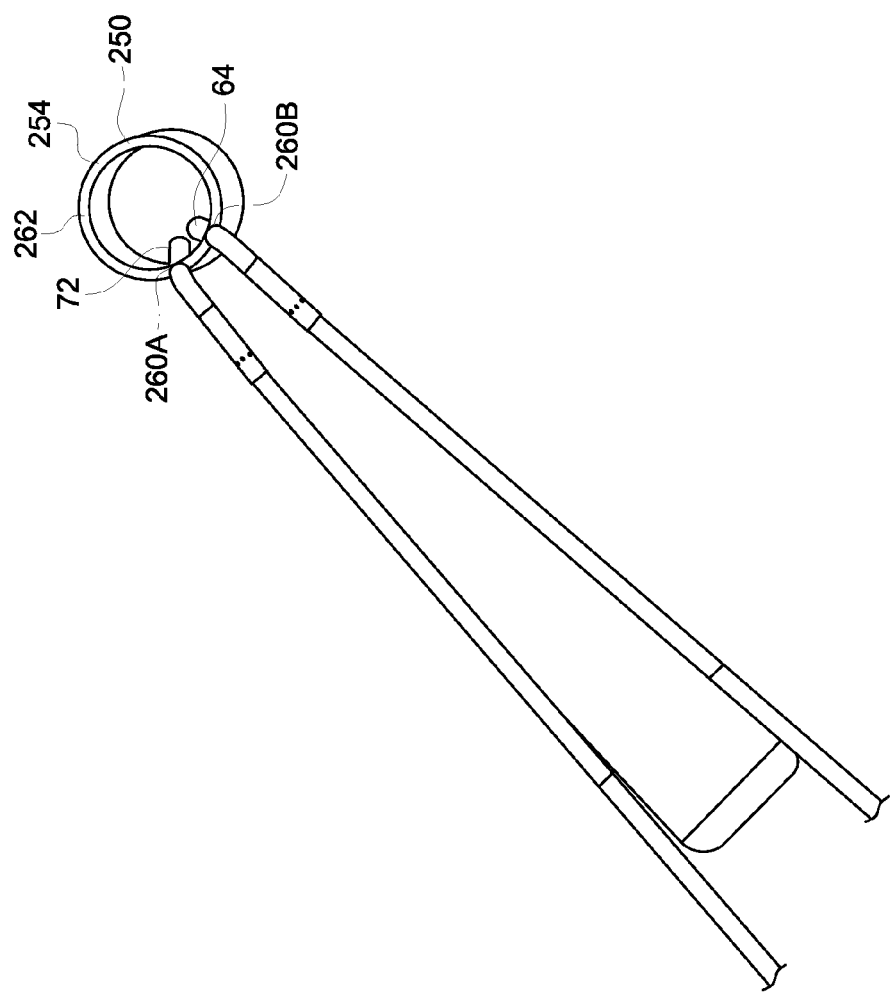

Referring to FIGS. 17A and 17B, in one embodiment, a surgical tool 250 has a tubular shaped body 254 with first and second elongated openings 260A, 260B extending through an outer wall 262. The first and second elongated openings are preferably adapted to receive respective first and second curved distal tips 64, 72 of a surgical illumination device as shown and described herein (e.g., FIGS. 1 and 15). In one embodiment the first and second elongated openings 260A, 260B may extend along respective axes that intersect one another so that the light emitted from the distal-most ends of the curved distal tips 64, 72 intersects. In one embodiment, the light generated by the LED is preferably projected toward the lower end 258 of the tubular shaped body 254 for illuminating a surgical site.

Figure 18A:
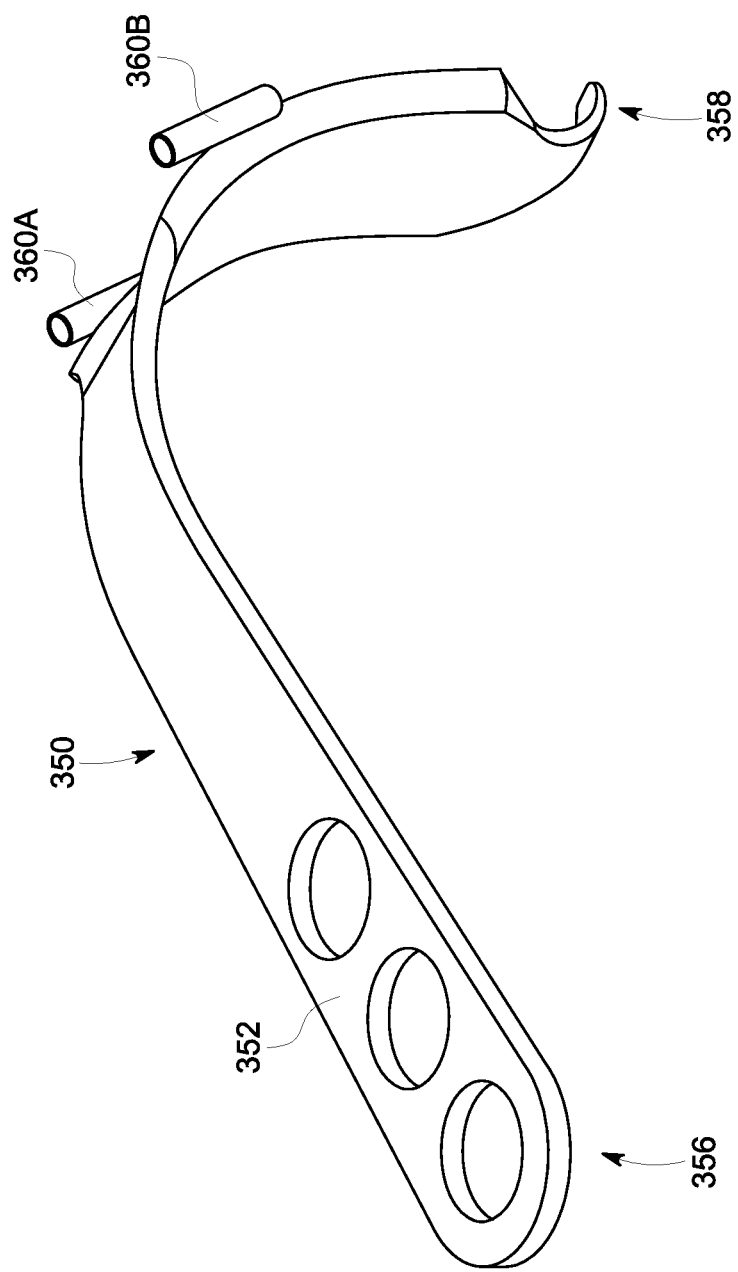
FIGS. 18A-18B and 19A-19C show a method of using the surgical illumination device of FIG. 15 to illuminate a surgical tool, in accordance with one embodiment of the present invention.
Figure 18B:
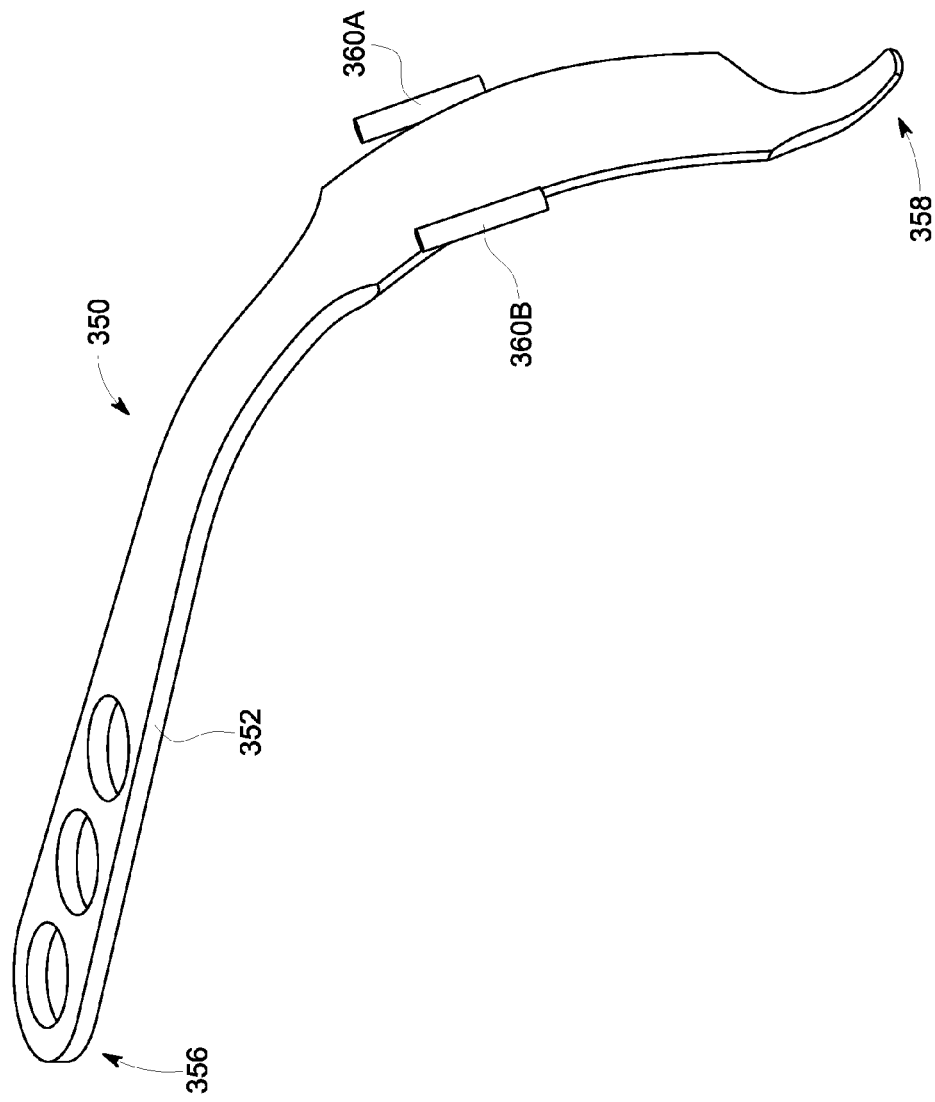

Referring to FIGS. 18A and 18B, in one embodiment, a surgical tool 350 preferably has a handle 352 at a proximal end 356 thereof and a distal working end 358. In one embodiment, the surgical tool 350 preferably includes a pair of elongated tubes 360A, 360B that are located on opposite lateral sides of the surgical tool. The elongated tubes 360A, 360B are preferably oriented toward the distal working end 358 of the surgical tool. The elongated tubes 360A, 360B preferably define cylindrical openings that conform to the outer surfaces of the stainless steel tubes of the distal tips.

Figure 19A:
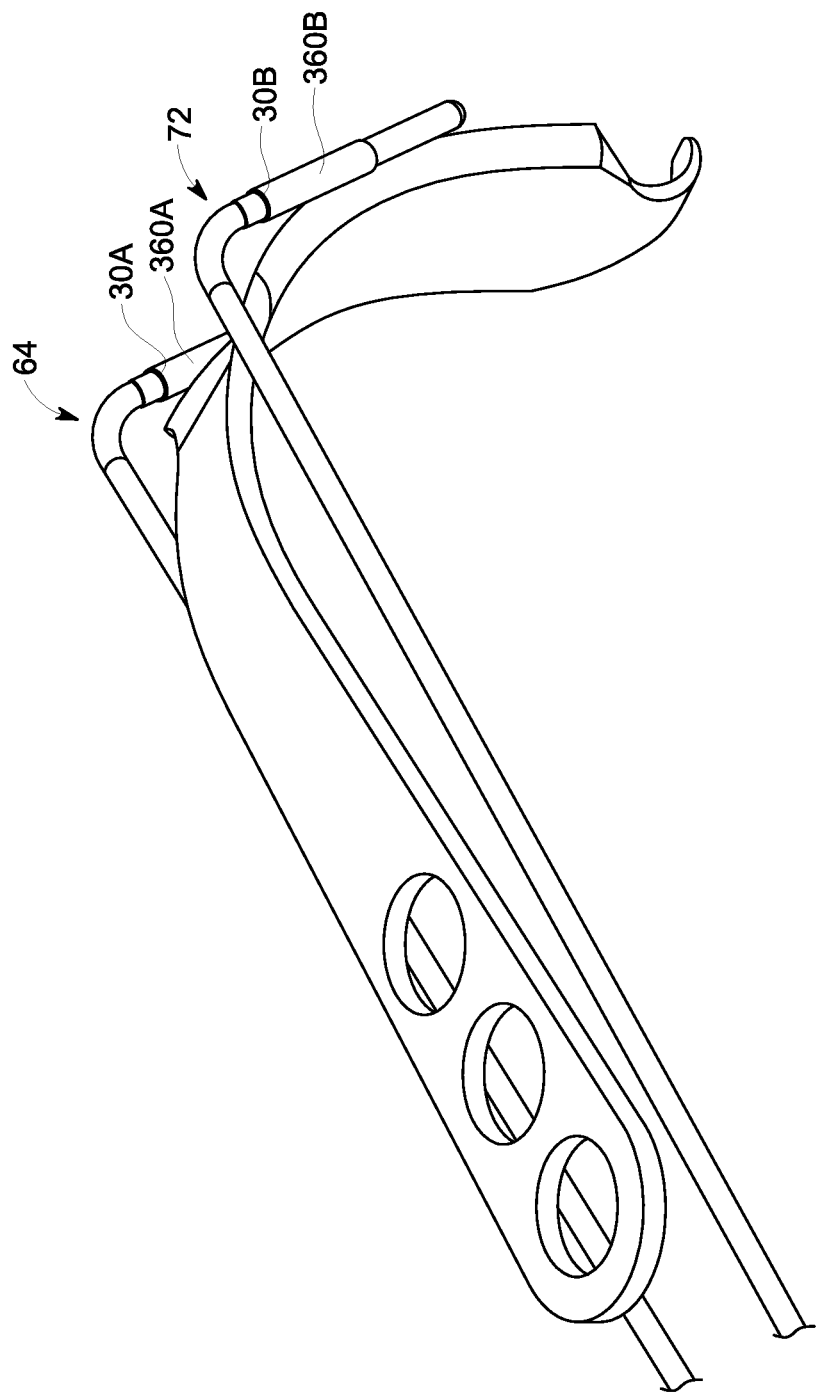
Figure 19B:
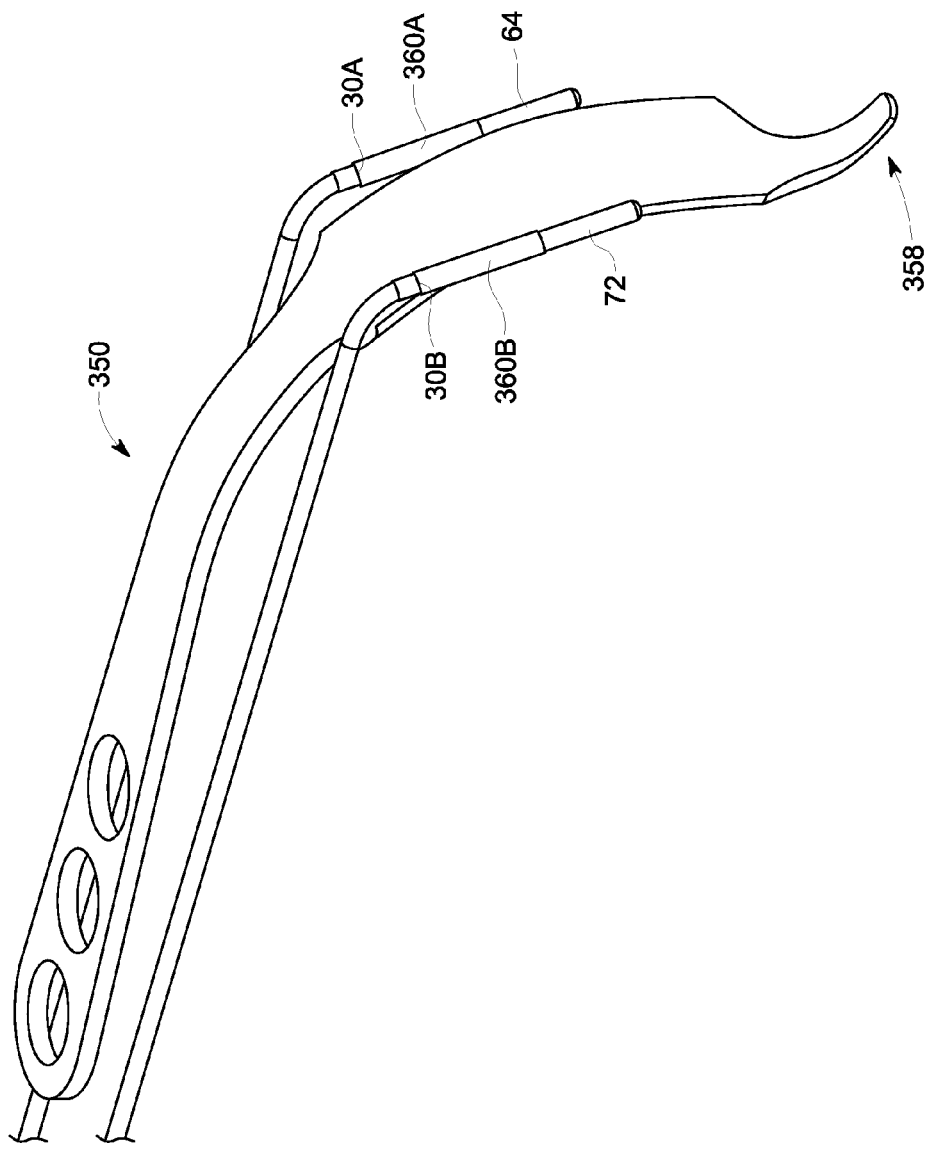
Figure 19C:
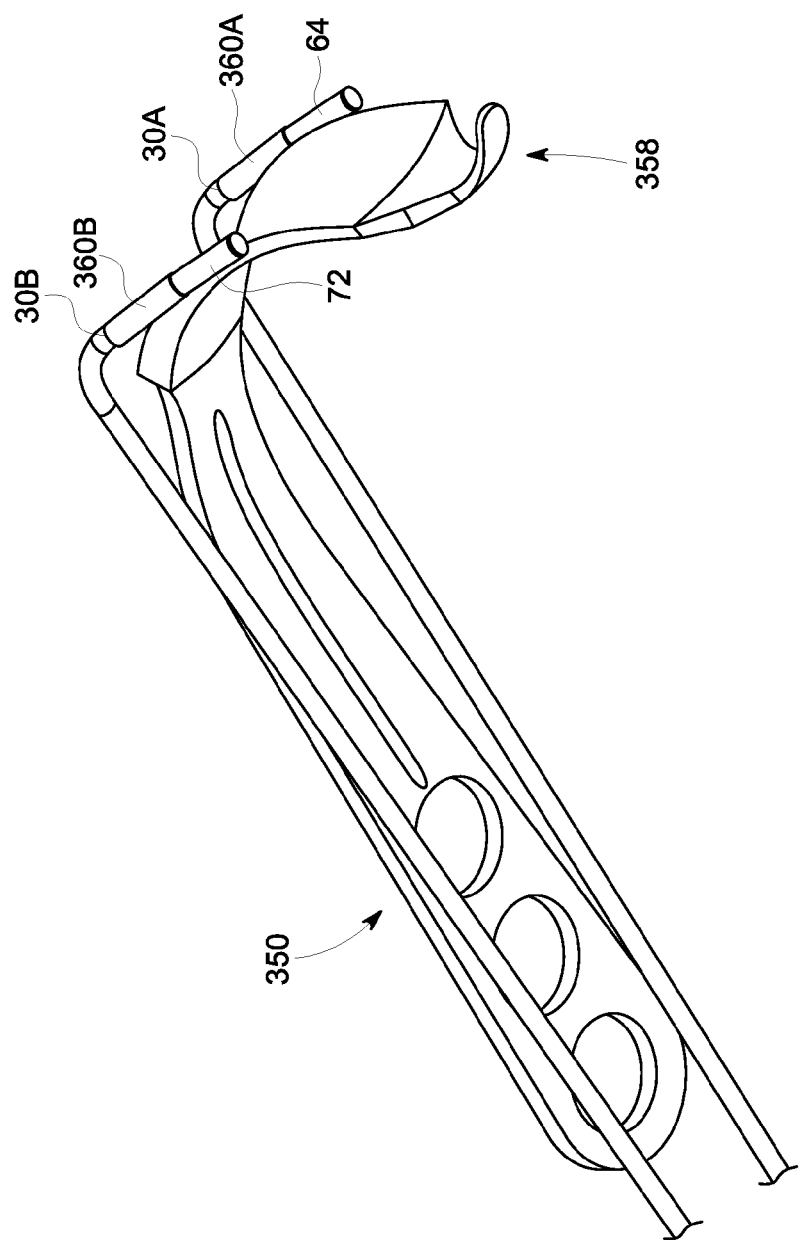

Referring to FIGS. 19A-19C, in one embodiment, the first curved distal tip 64 is inserted into the first elongated tube 360A. A stop flange 30A on the first curved distal tip 64 has an outer diameter that is larger than the inner diameter of the first elongated tube for halting distal sliding movement of the distal tip 64 relative to the first elongated tube 360A. In one embodiment, the second curved distal tip 72 is preferably inserted into the second elongated tube 360B. A stop flange 30B on the second curved distal tip 72 has an outer diameter that is larger than the inner diameter of the second elongated tube for halting distal sliding movement of the distal tip 72 relative to the second elongated tube 360B. When the surgical illumination device is activated, the first and second curved distal tips 64, 72 preferably project LED generated light toward the distal working end 358 of the surgical tool 350 for illuminating the distal end of the surgical tool and/or a surgical site.

Figure 20:
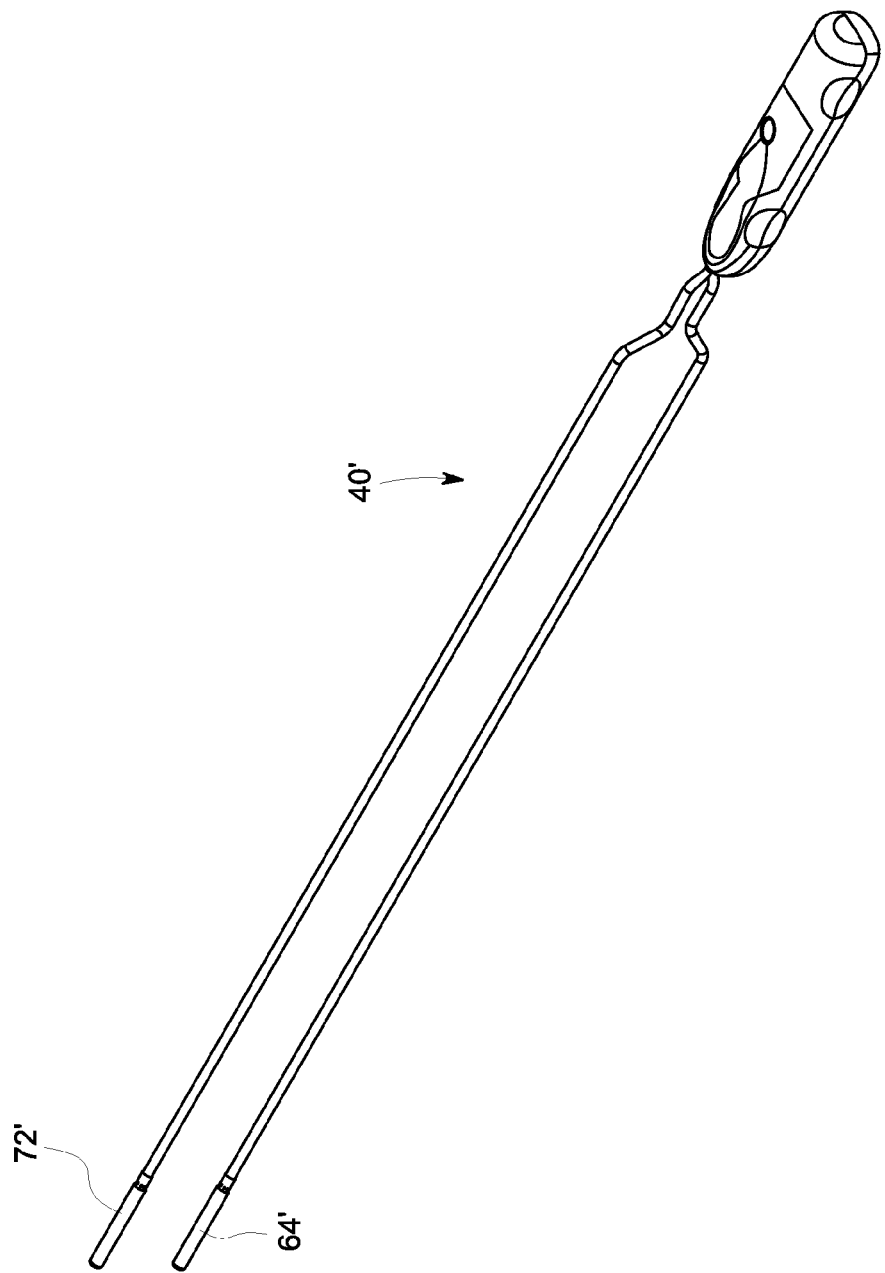
FIG. 20 shows a perspective view of a surgical illumination device for illuminating surgical tools and surgical sites, in accordance with one embodiment of the present invention.

Referring to FIG. 20, in one embodiment, a surgical illumination tool 40' similar to that shown and described herein has straight distal tips 64', 72' rather than curved distal tips (FIG. 1). The distal tips 64', 72' are preferably constructed as shown and described herein, however, the stainless steel tubes and the heat sinks disposed inside the stainless steel tubes are not bent or curved.

Referring to FIGS. 21A-21D, in one embodiment, a surgical tool 450 has a handle 452 at a proximal end 456 and a distal working end 458. The surgical tool 450 preferably has a first elongated opening 460A adapted to receive the first straight distal tip 64' (FIG. 20) and a second elongated opening 460B adapted to receive the second straight distal tip 72' (FIG. 20). The elongated openings 460A, 460B preferably define elongated cylindrical paths having cross-sections that closely match the cylindrical shapes of the straight distal tips 64', 72' so that when the tips are inserted into the elongated openings 460A, 460B, the tips do not shift and/or move relative to the elongated openings. In one embodiment, the light emitted by the distal tips 64', 72' is desirably oriented toward the distal working end 458 of the surgical tool 450 for illuminating the distal end of the surgical tool and/or a surgical site.

Figure 21A:
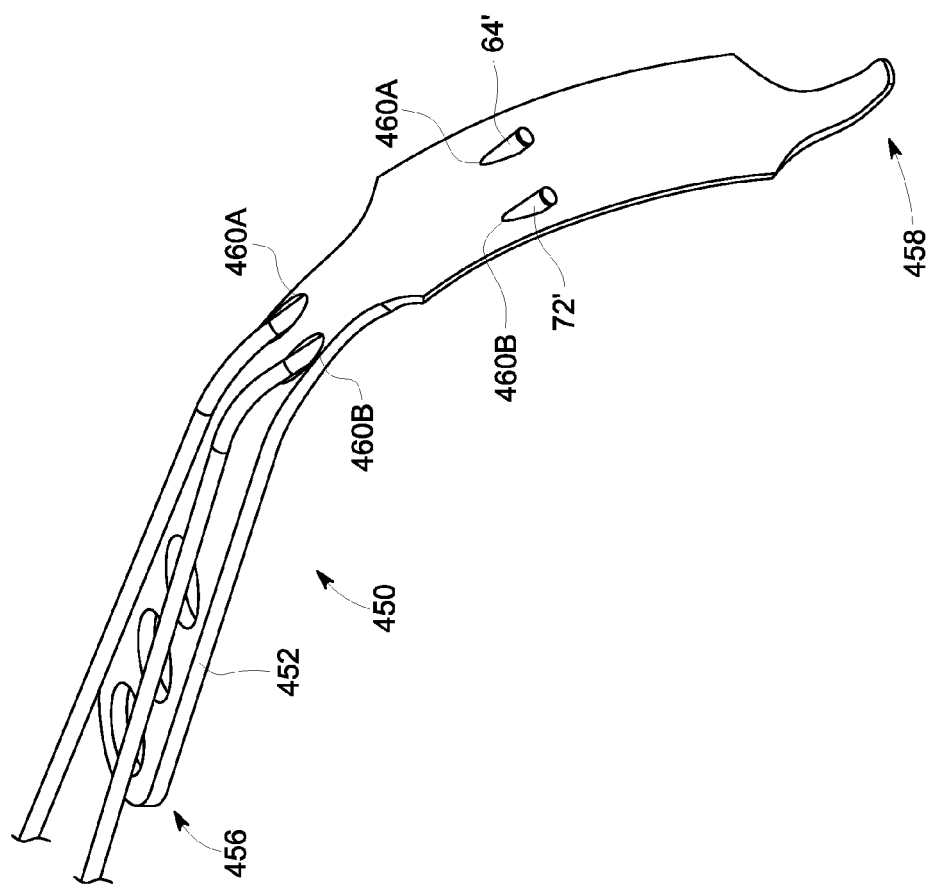
FIGS. 21A-21D show a method of using the surgical illumination device of FIG. 20 to illuminate a surgical tool, in accordance with one embodiment of the present invention.
Figure 21B:
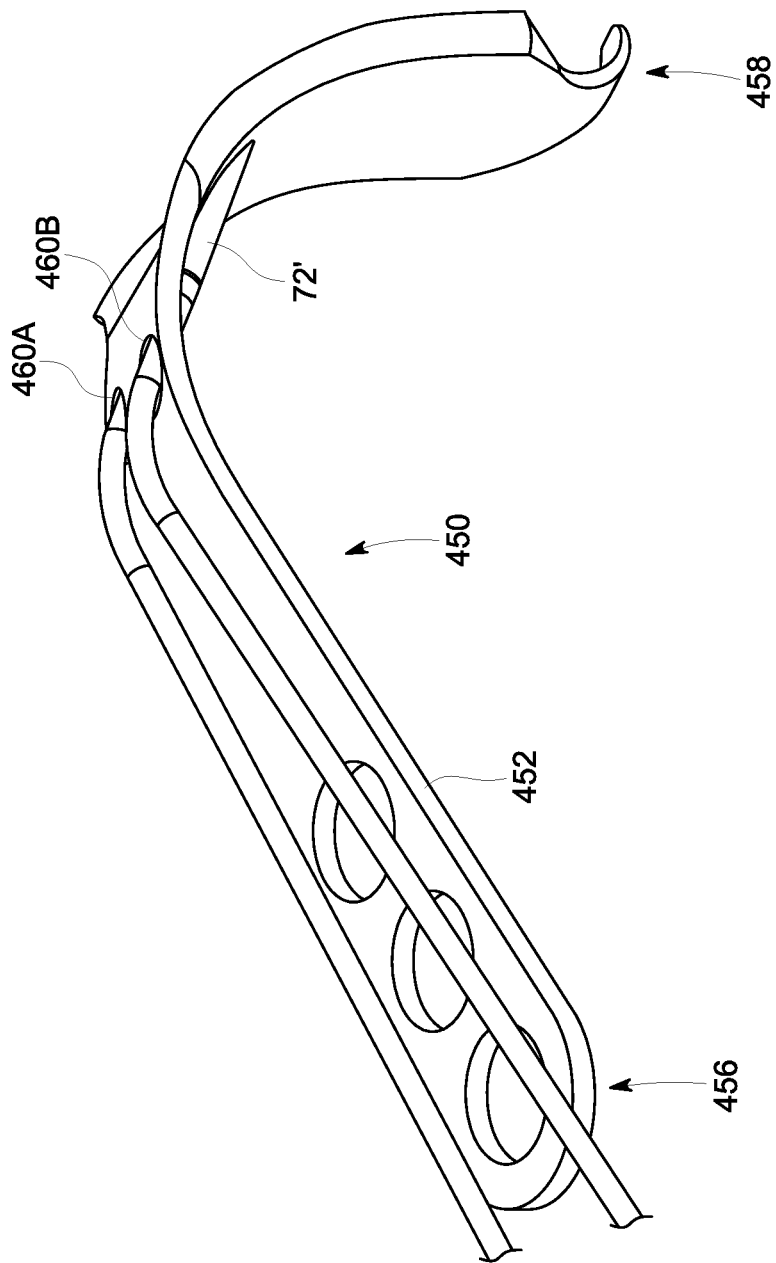
Figure 21C:
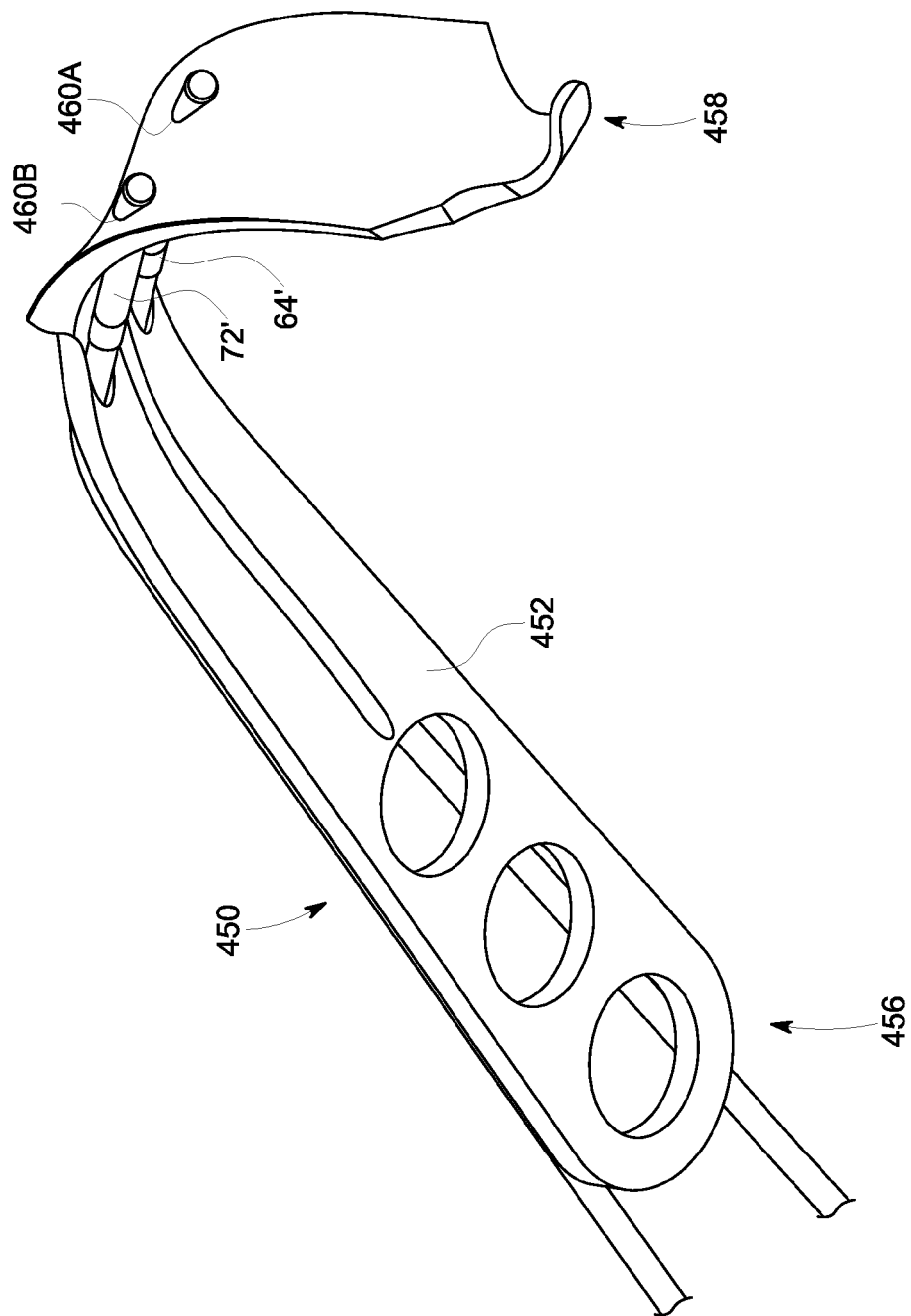
Figure 21D:
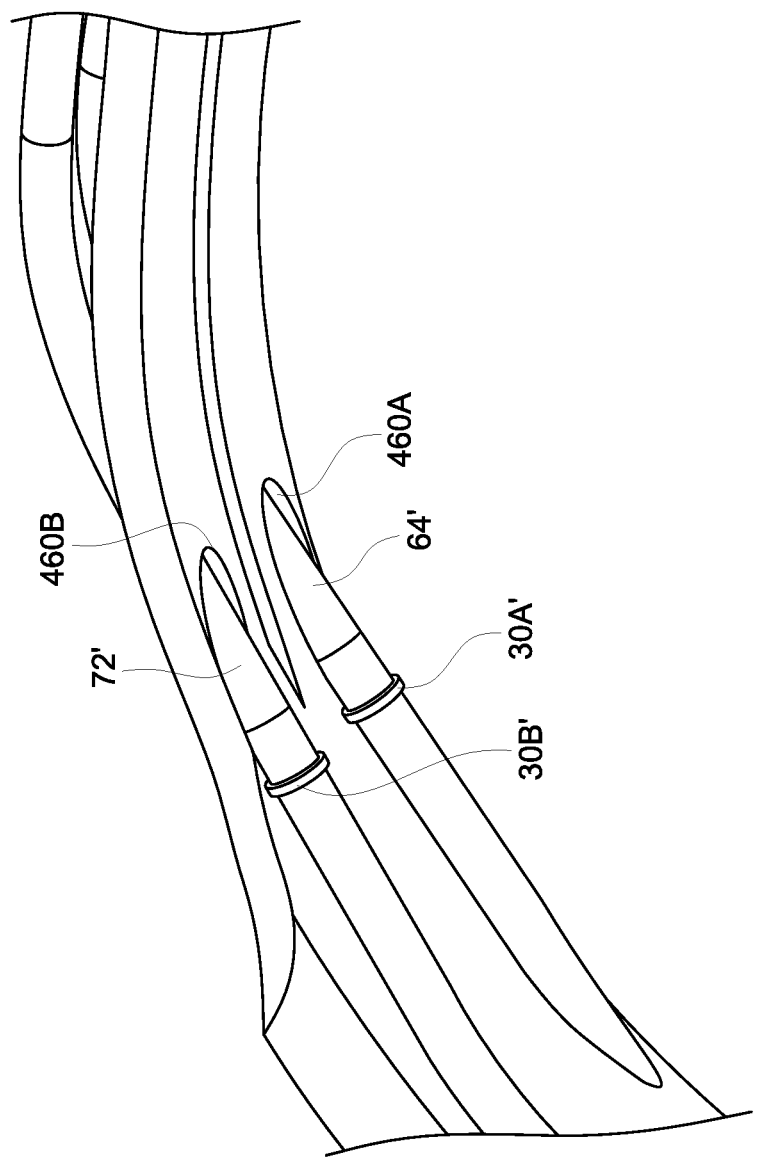

Referring to FIG. 21D, in one embodiment, annular stop 30A', 30B' are provided on the respective stainless steel tubes of the distal tips 64', 72' for halting distal sliding movement of the distal tips relative to the respective elongated openings 460A, 460B.

Figure 22:
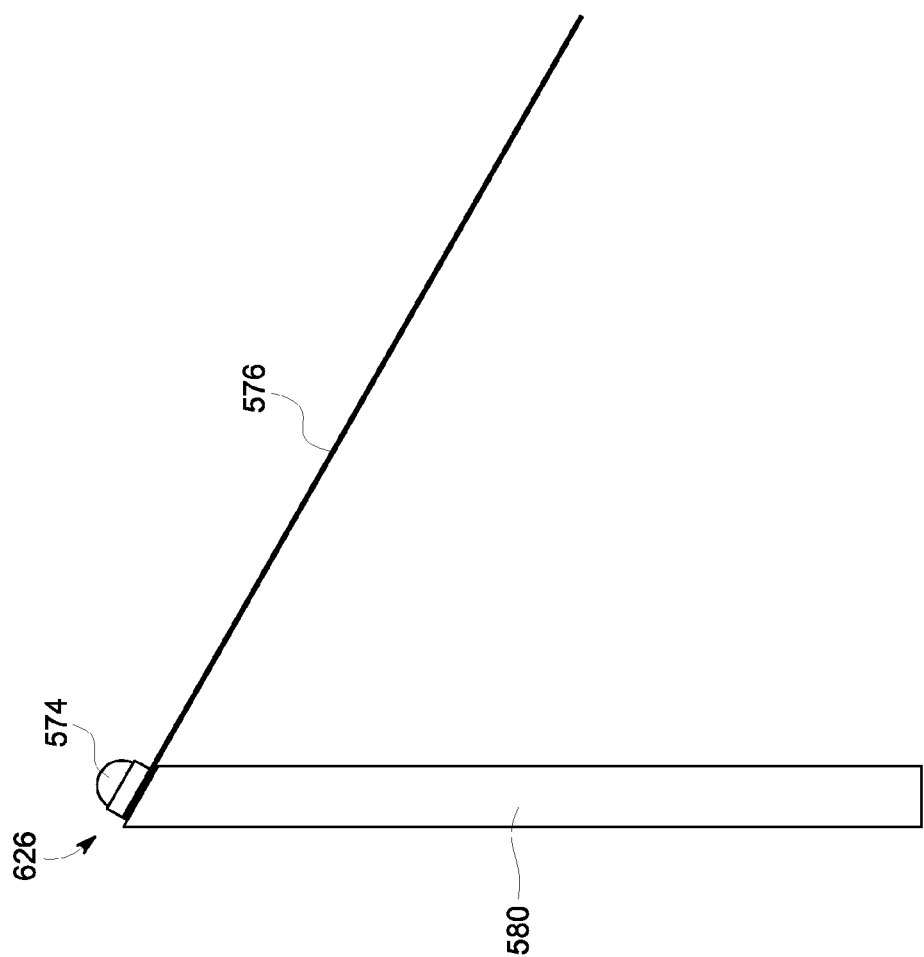
FIG. 22 shows a heat sink having a sloping distal end face and a LED and flexible circuit subassembly secured to the sloping distal end face, in accordance with one embodiment of the present invention.

Referring to FIG. 22, in one embodiment, a surgical illumination device preferably includes a heat sink 580 having a sloping distal end face 626 with an LED 574 mounted over the sloping distal end face 626. In one embodiment, the LED 574 is electrically interconnected with a flexible circuit 576 and the subassembly including the LED is mounted onto the sloping distal end face 626 of the heat sink 580. In one embodiment, the structure shown in FIG. 22 may be utilized for providing a surgical illumination device that directs light in a lateral direction. In other embodiments, the angle of the sloping distal end face may be modified for different uses.

Figure 23:
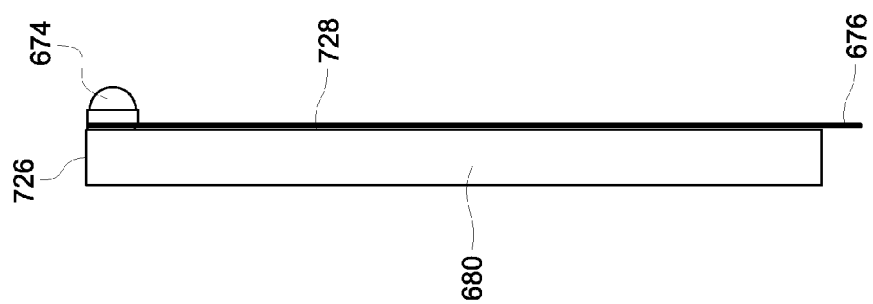
FIG. 23 shows a heat sink having an elongated flat surface that extends between a proximal end to distal end of the heat sink and a LED and flexible circuit subassembly secured to the elongated flat surface of the heat sink, in accordance with one embodiment of the present invention.

Referring to FIG. 23, in one embodiment, a surgical illumination device preferably includes a heat sink 680 having a proximal end face 722, a distal end face 726, and an elongated flat surface 728 that extends between the proximal and distal ends. In one embodiment, an LED 674 is mounted over the elongated flat surface 728. In one embodiment, the LED 674 is electrically interconnected with a flexible circuit 676 and the subassembly including the LED is mounted onto the elongated flat surface 728 of the heat sink 680. In one embodiment, the structure shown in FIG. 23 may be utilized for providing a surgical illumination device that directs light in a lateral direction.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A surgical illumination device comprising:
   a LED including a base having a bottom surface with a positive terminal, a negative terminal, and a heat transfer pad;
   a flexible circuit including a flexible dielectric substrate with a proximal end, a distal end, and first and second electrically conductive traces extending from said proximal end to said distal end;
   said distal end of said flexible dielectric substrate including said first conductive trace electrically interconnected with said positive terminal, said second conductive trace electrically interconnected with said negative terminal, and a heat transfer window aligned with said heat transfer pad of said LED base;
   a heat sink having a proximal end and a distal end with a distal end face;
   a thermally conductive adhesive pad disposed between said distal end of said dielectric substrate and said distal end face of said heat sink for securing said LED and said distal end of said dielectric substrate to said distal end face of said heat sink, wherein said thermally conductive adhesive pad is aligned with said heat transfer window of said dielectric substrate and said heat transfer pad of said LED base;
   an elongated tube having a proximal end and a distal end, wherein said LED, said flexible circuit and said heat sink are disposed inside said elongated tube, and wherein said elongated tube comprises an indented section formed in an outer surface thereof;
   wherein said elongated tube comprises an elongated conduit extending from said proximal end to said distal end of said elongated tube, wherein said LED, said flexible circuit and said heat sink are disposed inside said elongated conduit of said elongated tube with said LED being located adjacent said distal end of said elongated tube;
   wherein said indented section of said elongated tube is visible outside said elongated tube and projects into said elongated conduit for controlling the orientation of said heat sink inside said elongated tube, wherein said elongated flat surface of said heat sink faces toward said indented section of said elongated tube for limiting rotation of said heat sink about the longitudinal axis of said heat sink.

2. The device as claimed in claim 1, wherein said distal end of said dielectric substrate comprises a LED mounting pad having a top surface and a bottom surface, wherein said first and second conductive traces are accessible at said top surface of said LED mounting pad, and wherein said heat transfer window extends from said top surface to said bottom surface of said LED mounting pad.

3. The device as claimed in claim 2, wherein said heat transfer pad of said LED base is located between said positive and negative terminals, and wherein said heat transfer window of said LED mounting pad is located between said first and second conductive traces.

4. The device as claimed in claim 2, wherein said LED base has an outer perimeter and said LED mounting pad has an outer perimeter that matches the outer perimeter of said LED base.

5. The device as claimed in claim 1, wherein said heat sink has an elongated flat surface that extends from said distal end face to said proximal end of said heat sink, and wherein both said first conductive trace electrically interconnected with said positive terminal and said second conductive trace electrically interconnected with said negative terminal overlie said elongated flat surface of said heat sink.

6. The device as claimed in claim 5, wherein said LED mounting pad of said dielectric substrate is secured over said distal end face of said heat sink and an intermediate section of said dielectric substrate overlies said elongated flat surface of said heat sink.

7. The device as claimed in claim 6, wherein said distal end face of said heat sink is perpendicular to said elongated flat surface of said heat sink, wherein said heat sink comprises copper, and wherein said LED base covers an area of 6mm$^2$, said distal end face of said heat sink covers an area of 7-9 mm$^2$, and said heat sink has a length of 35-36 mm.

8. The device as claimed in claim 7, wherein said distal end of said heat sink comprises an edge located between said distal end face and said elongated flat surface of said heat sink, and wherein said flexible dielectric substrate is folded over said edge.

9. The device as claimed in claim 8, wherein said distal end face of said heat sink defines a flat surface and said proximal end of said heat sink comprises a proximal end face that is flat.

10. The device as claimed in claim 9, wherein said proximal end of said heat sink comprises a proximal edge located between said proximal end face and said elongated flat surface of said heat sink, and wherein said proximal end of said flexible dielectric substrate is folded over said proximal edge of said heat sink.

11. The device as claimed in claim 1, wherein said elongated tube and said heat sink are bent between said proximal and distal ends thereof, respectively, with said indented section of said bent elongated tube being located on said concave side of said bent elongated tube and said convexly curved side of said bent elongated tube facing away from said indented section.

12. The device as claimed in claim 1, wherein said elongated tube comprises stainless steel, said device further comprising an optical lens secured to said distal end of said elongated tube for covering said LED.

13. The device as claimed in claim 1, further comprising a flexible power cord electrically interconnected with said first and second conductive traces of said flexible circuit, wherein a distal end of said flexible power cord is inserted into an opening at said proximal end of said elongated tube.

14. The device as claimed in claim 13, wherein said flexible power cord comprises:
   a first conductive wire having a non-conductive outer cladding, said first conductive wire having a proximal end, and a distal end electrically interconnected with said first conductive trace at said proximal end of said flexible dielectric substrate;

a second conductive wire having a non-conductive outer cladding, said second conductive wire having a proximal end, and a distal end electrically interconnected with said second conductive trace at said proximal end of said flexible dielectric substrate.

15. The device as claimed in claim 14, further comprising a printed circuit board electrically interconnected with said first and second conductive wires, wherein said printed circuit board includes electronic components for controlling operation of said LED and at least one switch for activating said LED.

16. A surgical illumination device comprising:
a housing including a circuit board, a power source, and a switch for activating said surgical illumination device;
a flexible power line having a proximal end electrically interconnected with said circuit board and a distal end remote therefrom;
a distal tip secured to said distal end of said flexible power line, said distal tip comprising a LED having a base including a bottom surface with a positive terminal, a negative terminal, and a heat transfer pad,
a flexible circuit including a flexible dielectric substrate with a proximal end, a distal end, and first and second electrically conductive traces extending from said proximal end to said distal end of said flexible dielectric substrate;
said distal end of said flexible dielectric substrate including said first conductive trace electrically interconnected with said positive terminal, said second conductive trace electrically interconnected with said negative terminal, and a heat transfer window aligned with said heat transfer pad of said LED base;
a heat sink having a proximal end, a distal end with a distal end face, and an elongated flat surface that extends from said distal end face to said proximal end of said heat sink, wherein both said first conductive trace electrically interconnected with said positive terminal and said second conductive trace electrically interconnected with said negative terminal overlie said elongated flat surface of said heat sink;
a thermally conductive adhesive pad disposed between said distal end of said dielectric substrate and said distal end face of said heat sink for securing said LED and said distal end of said dielectric substrate to said distal end face of said heat sink, wherein said thermally conductive adhesive pad is aligned with said heat transfer window of said dielectric substrate and said heat transfer pad of said LED base;
a stainless steel tube having a proximal end, a distal end, and an elongated conduit extending from said proximal end to said distal end, wherein said LED, said flexible circuit and said heat sink are disposed inside said stainless steel tube with said LED being located adjacent said distal end of said stainless steel tube, and wherein said stainless steel tube comprises an indented section formed in an outer surface thereof;
wherein said indented section of said stainless steel tube is visible outside said stainless steel tube and projects into said elongated conduit for controlling the orientation of said heat sink inside said stainless steel tube, wherein said elongated flat surface of said heat sink faces toward said indented section of said stainless steel tube;
and an optical lens secured to said distal end of said stainless steel tube.

17. The device as claimed in claim 16, wherein said distal end of said dielectric substrate comprises a LED mounting pad having a top surface and a bottom surface, wherein said first and second conductive traces are accessible at said top surface of said LED mounting pad, wherein said heat transfer window extends from said top surface to said bottom surface of said LED mounting pad, wherein said heat transfer pad of said LED base is located between said positive and negative terminals of said LED, wherein said heat transfer window of said LED mounting pad is located between said first and second conductive traces, and wherein said LED base has an outer perimeter and said LED mounting pad has an outer perimeter that matches the outer perimeter of said LED base.

18. The device as claimed in claim 6, wherein said LED base is positioned atop said distal end face of said heat sink, and wherein a section of said LED base overhangs said elongated flat surface of said heat sink.

19. A surgical illumination device comprising:
a LED including a base having a bottom surface with a positive terminal, a negative terminal, and a heat transfer pad;
a flexible circuit including a flexible dielectric substrate with a proximal end, a distal end, and first and second electrically conductive traces extending from said proximal end to said distal end;
said distal end of said flexible dielectric substrate including said first conductive trace electrically interconnected with said positive terminal, said second conductive trace electrically interconnected with said negative terminal, and a heat transfer window aligned with said heat transfer pad of said LED base;
a heat sink having a proximal end and a distal end with a distal end face, wherein said heat sink has an elongated flat surface that extends from said distal end face to said proximal end of said heat sink, and wherein both said first conductive trace electrically interconnected with said positive terminal and said second conductive trace electrically interconnected with said negative terminal overlie said elongated flat surface of said heat sink;
a thermally conductive adhesive pad disposed between said distal end of said dielectric substrate and said distal end face of said heat sink for securing said LED and said distal end of said dielectric substrate to said distal end face of said heat sink, wherein said thermally conductive adhesive pad is aligned with said heat transfer window of said dielectric substrate and said heat transfer pad of said LED base;
an elongated outer tube having a proximal end and a distal end, wherein said LED, said flexible circuit and said heat sink are disposed inside said elongated outer tube, and wherein said elongated outer tube comprises an indented section formed in an outer surface of said elongated outer tube that opposes said elongated flat surface of said heat sink and that is visible outside said elongated outer tube, wherein said indented section projects into said elongated conduit for controlling the orientation of said heat sink inside said elongated outer tube.

* * * * *